US012559475B2

(12) United States Patent
Liang et al.

(10) Patent No.: US 12,559,475 B2
(45) Date of Patent: Feb. 24, 2026

(54) TETRAZINE COMPOUND CAPABLE OF HAVING RAPID CYCLOADDITION REACTION WITH NON-STRAINED OLEFINIC BORONIC ACID AND BIOMEDICAL APPLICATION THEREOF

(71) Applicant: NANJING UNIVERSITY, Suzhou (CN)

(72) Inventors: Yong Liang, Suzhou (CN); Cheng Tang, Suzhou (CN); Jiafang Deng, Suzhou (CN)

(73) Assignee: NANJING UNIVERSITY, Jiangsu (CN)

( * ) Notice: Subject to any disclaimer, the term of this patent is extended or adjusted under 35 U.S.C. 154(b) by 0 days.

(21) Appl. No.: 19/023,371

(22) Filed: Jan. 16, 2025

(65) Prior Publication Data

US 2025/0250250 A1 Aug. 7, 2025

(30) Foreign Application Priority Data

Feb. 6, 2024 (CN) ......................... 202410167131.2

(51) Int. Cl.

| | |
|---|---|
| ***C07D 401/14*** | (2006.01) |
| ***A61K 31/69*** | (2006.01) |
| ***A61K 47/22*** | (2006.01) |
| ***C07D 401/04*** | (2006.01) |

(52) U.S. Cl.

CPC ............ *C07D 401/14* (2013.01); *A61K 31/69* (2013.01); *A61K 47/22* (2013.01); *C07D 401/04* (2013.01)

(58) Field of Classification Search

None

See application file for complete search history.

(56) References Cited

PUBLICATIONS

Saghatforoush et al. "Mononuclear, tetranuclear and polymeric cadmium(II) complexes with the 3,6-bis(2-pyridyl)-1,2,4,5-tetrazine ligand: Synthesis, crystal structure, spectroscopic and DFT studies" Polyhedron 119 (2016) 160-174. (Year: 2016).*

* cited by examiner

*Primary Examiner* — Adam C Milligan
*Assistant Examiner* — Jed A Kucharczk
(74) *Attorney, Agent, or Firm* — JCIPRNET

(57) ABSTRACT

Disclosed are a tetrazine compound capable of having rapid cycloaddition reaction with non-strained olefinic boronic acid and biomedical application thereof. The present disclosure synthesizes a novel tetrazine compound capable of having rapid bioorthogonal cycloaddition reaction with non-strained olefinic boronic acid. The tetrazine compound of the present disclosure exhibits good stability, addressing the common contradiction in the stability and reactivity of a bioorthogonal reagent of a bioorthogonal reaction. A bioorthogonal cycloaddition reaction between the tetrazine compound of the present disclosure and non-strained olefinic boronic acid is characterized by readily available raw material, good biocompatibility, and high stability, and has great potential for application in the biomedical field of disease treatment, such as labeling, antibody-drug conjugates, prodrug release, and protein-targeted degradation.

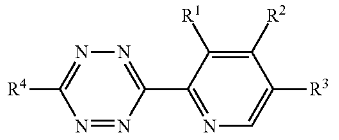

10 Claims, 8 Drawing Sheets

Tz-17

VBA-DOX

TETRAZINE COMPOUND CAPABLE OF HAVING RAPID CYCLOADDITION REACTION WITH NON-STRAINED OLEFINIC BORONIC ACID AND BIOMEDICAL APPLICATION THEREOF

CROSS-REFERENCE TO RELATED APPLICATION

This application claims the priority benefit of China application serial no. 202410167131.2, filed on Feb. 6, 2024. The entirety of the above-mentioned patent application is hereby incorporated by reference herein and made a part of this specification.

BACKGROUND

Technical Field

The present disclosure relates to compounds and application thereof, and particularly relates to a design, a preparation method and biomedical application of a novel tetrazine bioorthogonal reagent capable of rapid cycloaddition reaction with non-strained olefinic boronic acid.

Description of Related Art

Bioorthogonal reactions are considered to be ideal reactions for research on complex life systems due to their inherent chemical selectivity and adjustable reaction rates. At present, the widely used bioorthogonal cycloaddition reactions mainly include molecular ring strain-promoted azide-alkyne cycloaddition (SPAAC) reaction and inverse electron-demand diels-alder (IEDDA) reaction between tetrazine and strained alkene or alkyne. In the SPAAC reaction, strained alkyne is used to replace ordinary terminal alkyne, which eliminate the toxicity caused by a metal catalyst but reduces a rate of cycloaddition reaction. While the IEDDA reaction between tetrazine and strained alkene that is favored by researchers due to its extremely fast reaction kinetics has a high reactivity at the expense of the stability of reaction reagents. Therefore, developing non-strain-driven bioorthogonal reactions capable of balancing reaction kinetics and reagent stability has significant importance for scientific research in more complex life systems and has promising application in biomedicine.

SUMMARY

Objectives of the present disclosure: in order to solve the deficiencies in the prior art, the present disclosure aims to prepare a novel tetrazine compound with high stability and good reactivity, and to develop a rapid cycloaddition reaction between the novel tetrazine compound and non-strained olefinic boronic acid, and to provide application of the reaction.

Technical solution: in order to realize the above objective, the present disclosure adopts the following technical solution:

a tetrazine compound, or a tautomer and a pharmaceutically acceptable salt thereof, where a structure of the compound is represented by Formula (I):

I

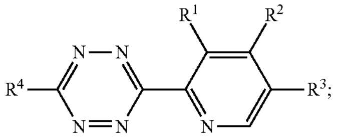

where:

$R^1$ is selected from $C_{1-3}$ alkyl;

$R^2$ is selected from hydroxyl, $C_{1-3}$ alkoxy, $C_{1-3}$ alkyl-amino;

$R^3$ is selected from H, $C_{1-3}$ alkyl, $C_{1-3}$ alkyl-hydrocarbon, $C_{1-3}$ alkyl-carboxylic acid, $C_{1-3}$ alkyl-amino, $C_{1-3}$ alkyl azide, $C_{1-3}$ alkyl alkyne;

$R^4$ is selected from H, $C_{1-3}$ alkyl, carboxyl, $C_{1-3}$ alkyl-carboxyl, amino, $C_{1-3}$ alkyl-amino, substituted or unsubstituted phenyl, substituted or unsubstituted six-membered heteroaryl, —O—CONH—$CH_2$-Ph, —$CH_2$—O—$CH_3$; and the substituted phenyl and the substituted six-membered heteroaryl are each independently substituted by the following groups: COOH, $CH_2COOH$, amino or $CH_2NH_2$. Further preferably, the amino or the amino in the $C_{1-3}$ alkyl-amino is protected with Boc.

The tetrazine compound, or a tautomer and the pharmaceutically acceptable salt thereof, $R^1$ is selected from $C_{1-3}$ alkyl;

$R^2$ is selected from hydroxyl, $C_{1-3}$ alkoxy, $C_{1-3}$ alkyl-amino;

$R^3$ is selected from H, $C_{1-3}$ alkyl, $C_{1-3}$ alkyl-hydrocarbon, $C_{1-3}$ alkyl-carboxylic acid, $C_{1-3}$ alkyl-amino, $C_{1-3}$ alkyl azide, $C_{1-3}$ alkyl alkyne;

$R^4$ is selected from H, $C_{1-3}$ alkyl, carboxyl, $C_{1-3}$ alkyl-carboxyl, amino, $C_{1-3}$ alkyl-amino, substituted or unsubstituted phenyl, substituted or unsubstituted six-membered heteroaryl, —O—CONH—$CH_2$-Ph, —$CH_2$—O—$CH_3$; the substituted phenyl and the substituted six-membered heteroaryl are each independently substituted by the following groups: COOH, $CH_2COOH$, amino or $CH_2NH_2$; and the amino or the amino in the $C_{1-3}$ alkyl-amino can be protected with Boc; and the six-membered heteroaryl is a six-membered nitrogen heteroaryl.

The tetrazine compound, or a tautomer and the pharmaceutically acceptable salt thereof, and the six-membered heteroaryl is pyridyl and pyrimidyl.

The tetrazine compound, or a tautomer and the pharmaceutically acceptable salt thereof, and the tetrazine compound is selected from one of the following structures:

Tz-1

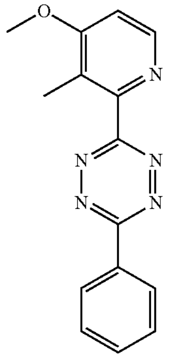

Tz-2
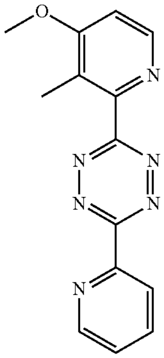
Tz-3
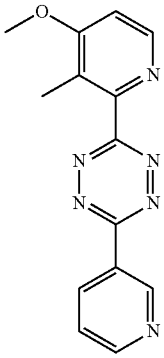
Tz-4
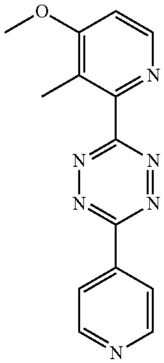
Tz-5
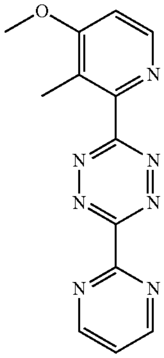
Tz-6
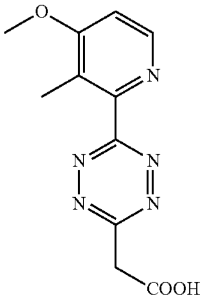
Tz-7
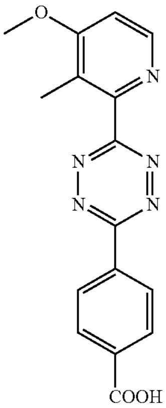
Tz-8
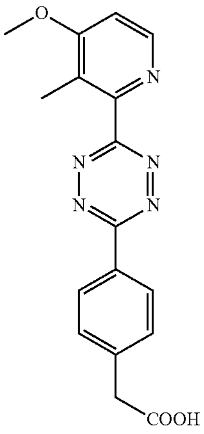
Tz-9
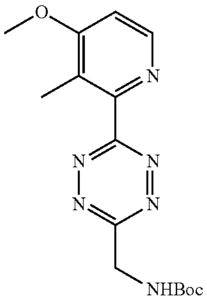

-continued
Tz-10
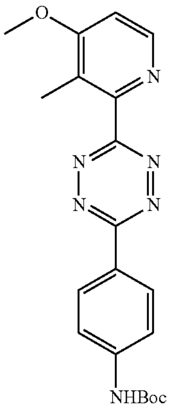
Tz-11
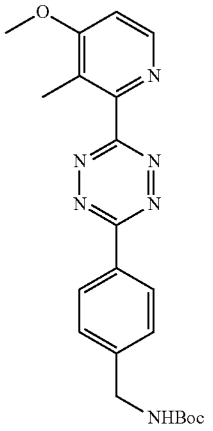
Tz-12
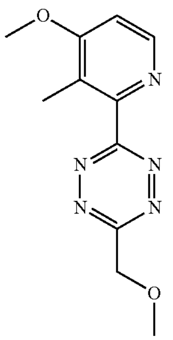
-continued
Tz-13
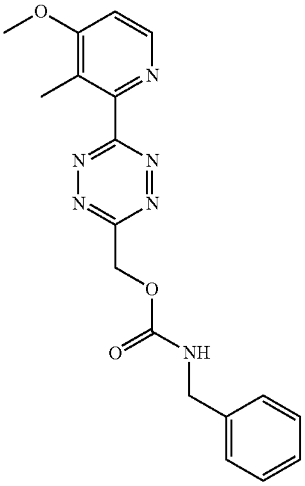
Tz-14
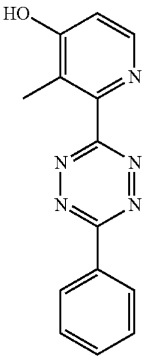
Tz-15
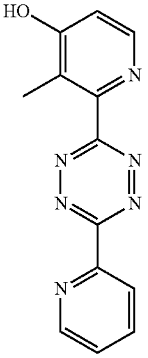
Tz-16
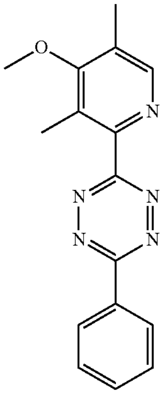

-continued
Tz-17
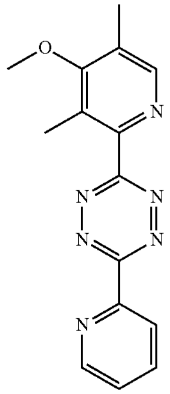
Tz-18
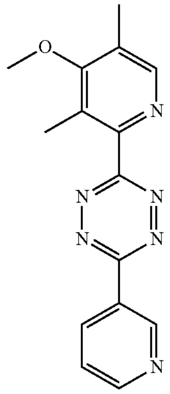
Tz-19
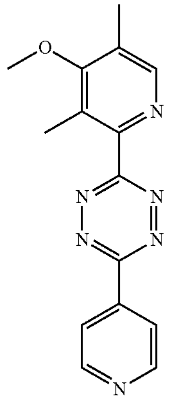
Tz-20
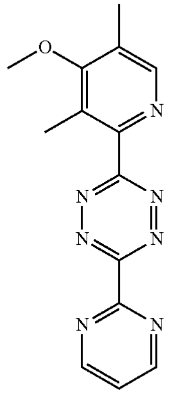
-continued
Tz-21
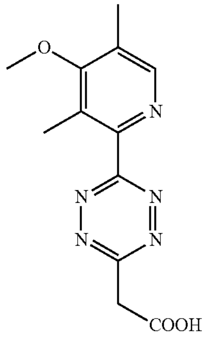
Tz-22
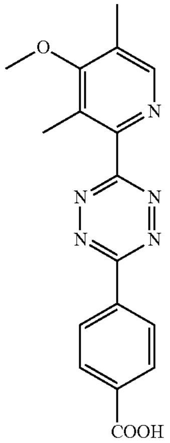
Tz-23
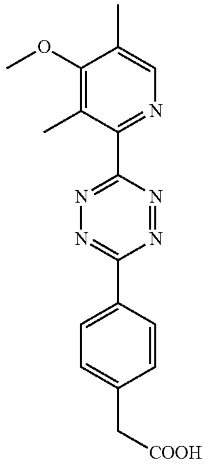
Tz-24
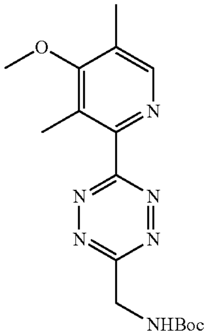

-continued
Tz-25
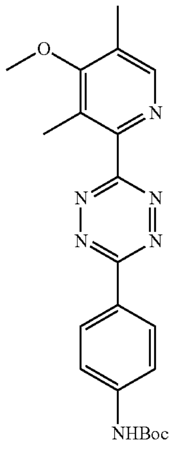
Tz-26
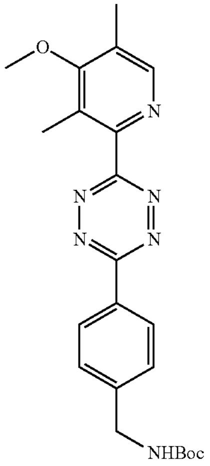
Tz-27
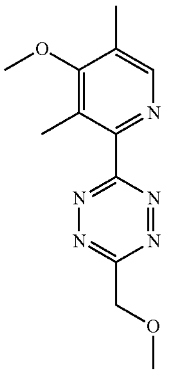
-continued
Tz-28
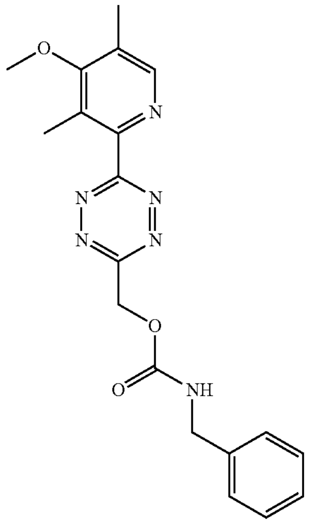
Tz-29
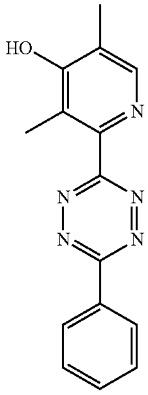
Tz-30
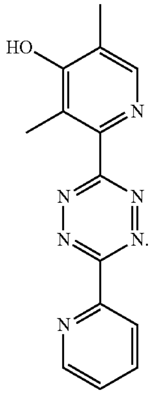
A method for preparing the tetrazine compound, or a tautomer and the pharmaceutically acceptable salt thereof, including the following steps:

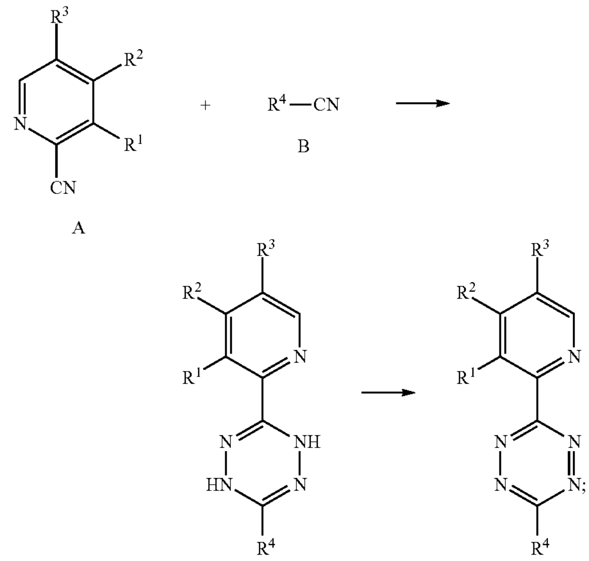

$R^1$, $R^2$, $R^3$ and $R^4$ are the same as described above.

Preferably, a feed equivalent ratio of Raw Material A to Raw Material B is 4:1-10:1.

Preferably, no solvent is used, or the solvent is ethanol.

Preferably, a reaction temperature is 40° C.-60° C.

The method for preparing the tetrazine compound, or a tautomer and the pharmaceutically acceptable salt thereof, and Raw Material A is selected from one of the following structures:

A-1

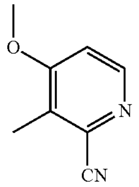

A-2

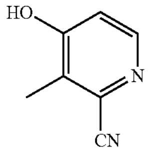

A-3

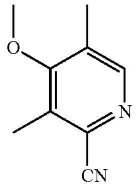

A-4

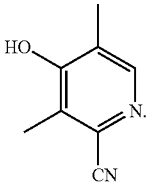

The method for preparing the tetrazine compound, or a tautomer and the pharmaceutically acceptable salt thereof, and Raw Material B is selected from one of the following structures:

B-1

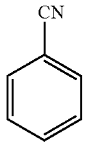

B-2

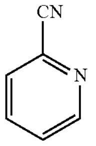

B-3

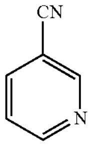

B-4

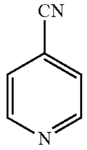

B-5

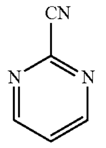

B-6

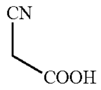

B-7

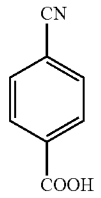

B-8

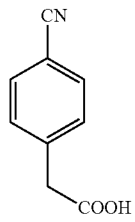

B-9

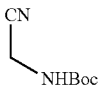

-continued

B-10

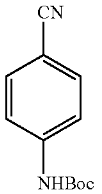

B-11

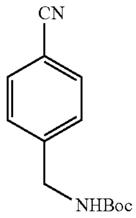

B-12

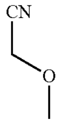

B-13

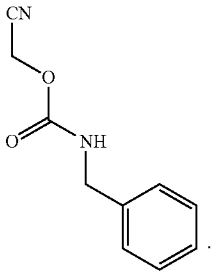

The tetrazine compound, or a tautomer and the pharmaceutically acceptable salt thereof, and a chemical equation of the tetrazine compound and the olefinic boronic acid is as follows:

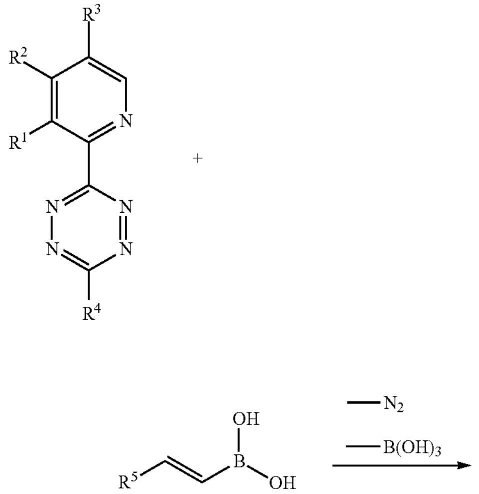

-continued

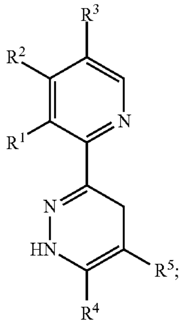

$R^1$, $R^2$, $R^3$ and $R^4$ are the same as described above. $R^5$ is selected from phenyl,

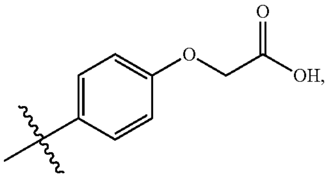

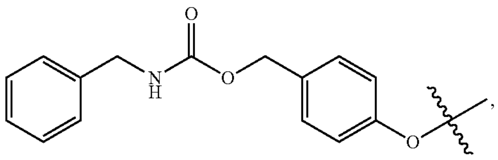

and

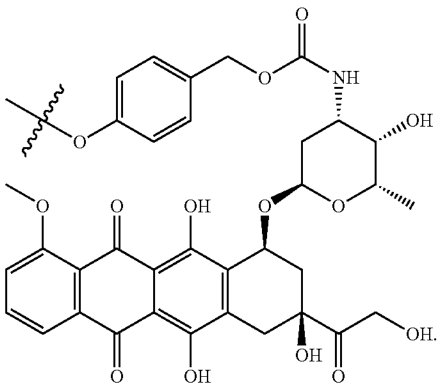 [SMILES: *Oc1ccc(COC(=O)N[C@H]2C[C@H](O[C@H]3C[C@](O)(C(=O)CO)Cc4c(O)c5c(c(O)c43)C(=O)c3c(OC)cccc3C5=O)O[C@@H](C)[C@H]2O)cc1]

Application of the tetrazine compound, or a tautomer and the pharmaceutically acceptable salt thereof in preparing labeling, antibody-drug conjugates, a prodrug delivery system or protein-targeted chimera technology.

In the application, the prodrug delivery system involves the reaction of the tetrazine compound, or a tautomer and a pharmaceutically acceptable salt thereof with olefinic boronic acid to release a drug for treatment;

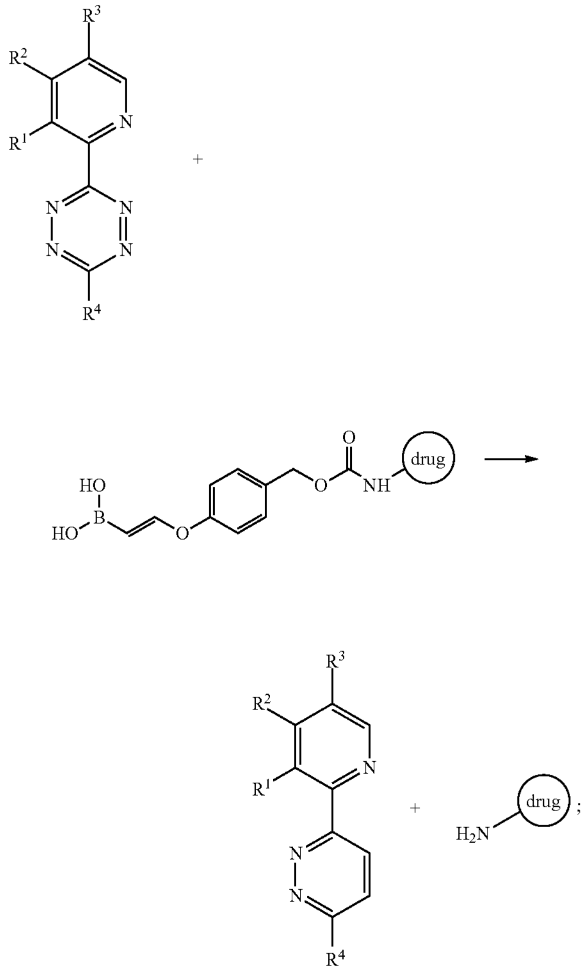

where $R^1$, $R^2$, $R^3$ and $R^4$ are the same as described above, and the drug represents a drug or a drug precursor.

In the application, the protein-targeted chimera technology is based on a bioorthogonal reaction between the tetrazine compound, a tautomer, or a pharmaceutically acceptable salt thereof, and olefinic boronic acid

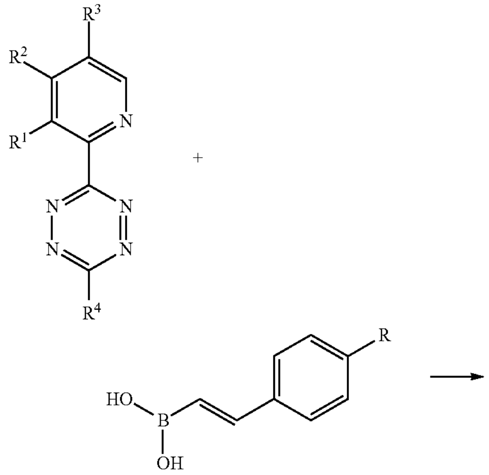

-continued

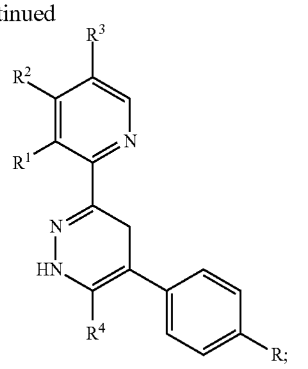

$R^1$, $R^2$ and $R^3$ are the same as described above, and R and $R^4$ represent targeting ligands in the protein-targeted chimera technology.

Beneficial effects: compared with the prior art, the present disclosure has the following advantages: (1) the tetrazine compounds of the present disclosure exhibit good stability and are less susceptible to decomposition by biological thiols in vivo, and the like. (2) The non-strained olefinic boronic acid reagents are easy to obtain, and exhibit good stability and high biocompatibility. (3) The bioorthogonal reaction between the tetrazine compounds and olefinic boronic acid of the present disclosure maintains reagent stability while ensuring high reaction kinetics. Experiments have verified the application of the tetrazine compounds in protein-targeted degradation in breast cancer. The tetrazine compounds of the present disclosure have great potential for application in the biomedical field of disease treatment, such as labeling, antibody-drug conjugates, prodrug release, and protein-targeted degradation. The tetrazine compounds of the present disclosure have great potential for application in the biomedical field of disease treatment, such as labeling, antibody-drug conjugates, prodrug release, and protein-targeted degradation.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

Figure 1:
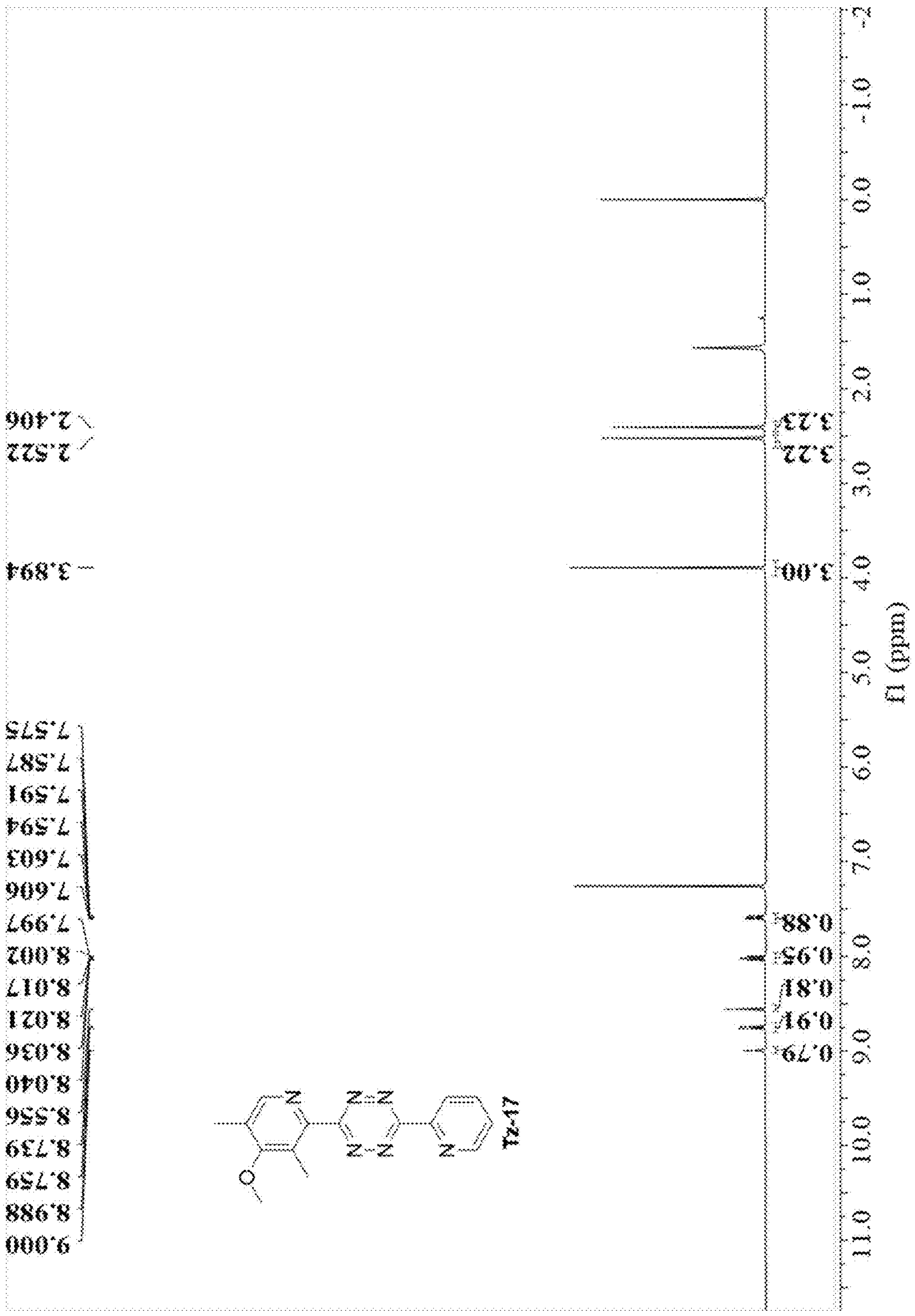
FIG. 1 is a nuclear magnetic resonance spectrum of a prepared novel tetrazine compound Tz-17.

The following examples are only used for exemplary illustration and explanation of the present disclosure, and should not be construed as limiting the scope of protection for the present disclosure. The technology completed based on the content mentioned above should fall within the scope of protection of the present disclosure.

Example 1

A method for preparing Compound Tz-2, including the following steps:

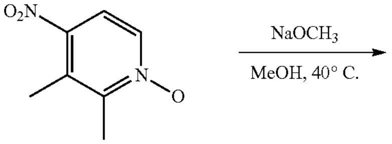

1

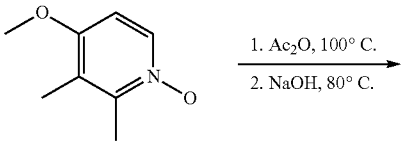

2

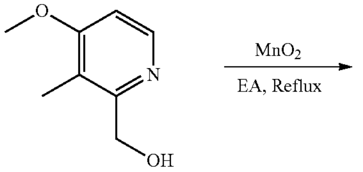

3

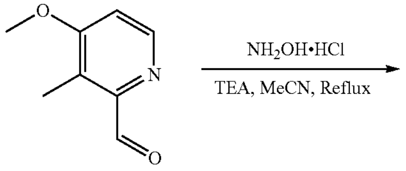

4

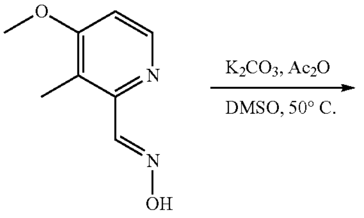

5

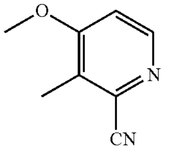

+

A-1

-continued

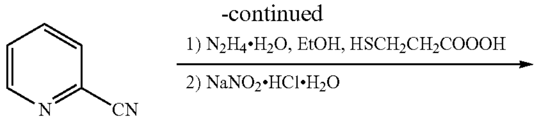

B-2

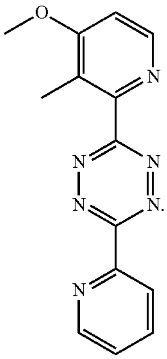

Tz-2

Step 1: Preparing Compound 2

2,3-dimethyl-4-nitropyridine-N-oxide (1.68 g, 10 mmol) and potassium carbonate (4.13 g, 30 mmol) were dissolved in 50 mL of methanol solution, and heated at 65° C. for reflux for 5 h, then filtered through diatomaceous earth, and column chromatography was performed to obtain 1.32 g of a white solid, that is, Compound 2, with a yield of 60%. $^1H$ NMR (400 MHz, $CDCl_3$) δ 8.14 (d, J=7.2 Hz, 1H), 6.62 (d, J=7.2 Hz, 1H), 3.85 (s, 3H), 2.51 (s, 3H), 2.17 (s, 3H). ESI-HRMS: $[M+H]^+$ calcd. For $[C_8H_{12}NO_2]^+$ m/z: 154.0862; found: 154.0861.

Step 2: Preparing Compound 3

Compound 2 (1.32 g, 8.6 mmol) was dissolved in 18 mL of acetic anhydride solution to obtain a mixture, the mixture was heated and stirred at 100° C. for 4 h, acetic anhydride was removed by rotary evaporation, 15 mL of a sodium hydroxide aqueous solution (2 mol/L) was then added, and heated at 90° C. for 4 h to be extracted with dichloromethane and dried with anhydrous sodium sulfate, and column chromatography was performed to obtain 0.825 g of a yellow solid, that is, Compound 3, with a yield of 70%. $^1H$ NMR (500 MHz, $CDCl_3$) δ 8.32 (d, J=5.7 Hz, 1H), 6.73 (d, J=5.7 Hz, 1H), 4.65 (s, 2H), 3.89 (s, 3H), 2.04 (s, 3H). ESI-HRMS: $[M-H]^-$ calcd. For $[C_8H_{10}NO_2]^-$ m/z: 152.0717; found: 152.0713.

Step 3: Preparing Compound 4

Compound 3 (500 mg, 3 mmol) was dissolved in 10 mL of ethyl acetate solution, and active manganese dioxide powder (1.318 g, 15 mmol) was added to obtain a mixture, a temperature of the mixture is raised to reflux and stirred overnight, and then filtered through diatomaceous earth, the ethyl acetate solution was removed by rotary evaporation, and column chromatography was performed to obtain 434 mg of a light yellow oil, that is, Compound 4, with a yield of 87%. $^1H$ NMR (500 MHz, $CDCl_3$) δ 10.19 (s, 1H), 8.54 (d, J=5.4 Hz, 1H), 6.90 (d, J=5.5 Hz, 1H), 3.93 (s, 3H), 2.52 (s, 3H). ESI-HRMS: $[M+H]^+$ calcd. For $[C_8H_{10}NO_2]^+$ m/z: 152.0706; found: 152.0701.

Step 4: Preparing Compound A-1

Compound 4 (434 mg, 2.6 mmol) was dissolved in 10 mL of acetonitrile solution, and hydroxylamine hydrochloride (218 mg, 3.1 mmol) and triethylamine (0.55 mL, 3.9 mmol) were added at 0° C. to obtain a mixture, the mixture was heated for reflux and stirred for 5 h, and acetonitrile was removed by rotary evaporation to obtain 468 mg of Compound 5.

Compound 5 (468 mg, 2.6 mmol) was dissolved in 8 mL of dimethyl sulfoxide solution under ice bath conditions, potassium carbonate (880 mg, 6.3 mmol) and acetic anhydride (0.6 mL, 6.3 mmol) were then added to obtain a mixture, the mixture was heated and stirred at 50° C. overnight, quenched with water, extracted with dichloromethane and then dried with anhydrous sodium sulfate, dimethyl sulfoxide was removed by rotary evaporation, and column chromatography was performed to obtain 375 mg of a white solid, that is, Compound A-1, with a yield of 87% over two steps. $^1$H NMR (500 MHz, $CDCl_3$) δ 8.40 (d, J=5.6 Hz, 1H), 6.90 (d, J=5.6 Hz, 1H), 3.92 (s, 3H), 2.40 (s, 3H). ESI-HRMS: $[M+H]^+$ calcd. For $[C_8H_9N_2O]^+$ m/z: 149.0709; found: 149.0704.

Step 5: Preparing Compound Tz-2

Compound A-1 (0.483 g, 3 mmol) and 2-cyanopyridine (1.25 g, 12 mmol) were dissolved in 2 mL of ethanol solution in a nitrogen atmosphere, 3-mercaptopropionic acid (0.3 mL, 3 mmol) was added first at 0° C., hydrazine hydrate (1.5 mL, 30 mmol) was then slowly added to obtain a mixture, and the mixture was heated to 50° C. and stirred for 24 h for reaction. After the mixture was cooled to room temperature, sodium nitrite and hydrochloric acid were added to the mixture under ice bath conditions and stirred for 30 min, extracted with dichloromethane, and dried with anhydrous sodium sulfate, ethanol was removed by rotary evaporation, and column chromatography was performed to obtain 0.234 g of a purple-red solid, that is, Compound Tz-2, with a yield of 25%. $^1$H NMR (400 MHz, $CDCl_3$) δ 9.00 (d, J=4.0 Hz, 1H), 8.75 (d, J=7.9 Hz, 1H), 8.64 (d, J=5.5 Hz, 1H), 8.02 (td, J=7.8, 1.8 Hz, 1H), 7.59 (ddd, J=7.6, 4.8, 1.1 Hz, 1H), 6.98 (d, J=5.6 Hz, 1H), 3.99 (s, 3H), 2.41 (s, 3H). ESI-HRMS: $[M+H]^+$ calcd. For $[C_{14}H_{13}N_6O]^+$ m/z: 281.1145; found: 281.1139.

Example 2

A method for preparing Compound Tz-17, including the following steps:

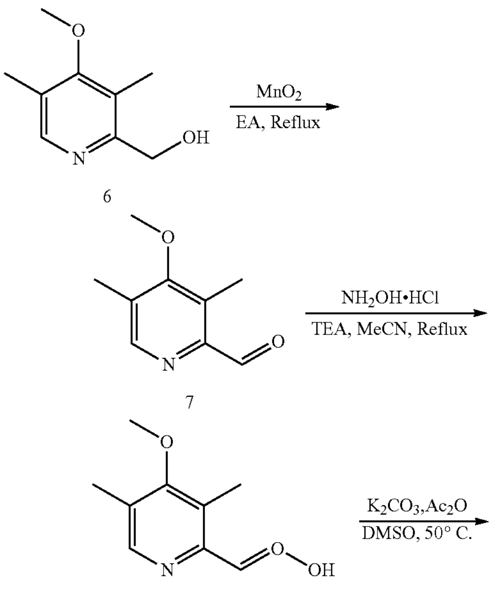

6

7

8

-continued

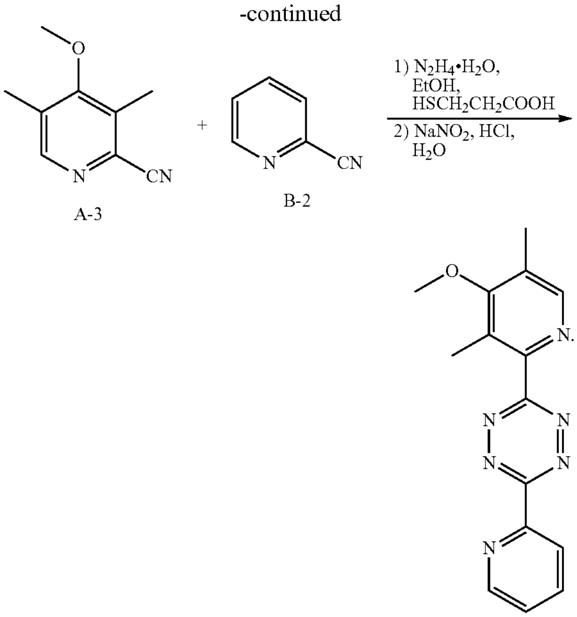

A-3

B-2

Tz-17

Step 1: Preparing Compound 7

4-methoxy-3,5-dimethyl-2-hydroxymethylpyridine (500 mg, 3 mmol) was dissolved in 10 mL of ethyl acetate solution, and active manganese dioxide powder (1.318 g, 15 mmol) was added to obtain a mixture, a temperature of the mixture is raised to reflux and stirred overnight, and then filtered through diatomaceous earth, the ethyl acetate solution was removed by rotary evaporation, and column chromatography was performed to obtain 434 mg of a light yellow oil, that is, Compound 7, with a yield of 88%. $^1$H NMR (400 MHz, $CDCl_3$) δ 10.14 (s, 1H), 8.45 (s, 1H), 3.80 (s, 3H), 2.57 (s, 3H), 2.35 (s, 3H). ESI-HRMS: $[M+H]^+$ calcd. For $[C_9H_{12}NO_2]^+$ m/z: 166.0863; found: 166.0858.

Step 2: Preparing Compound A-3

Compound 7 (434 mg, 2.6 mmol) was dissolved in 10 mL of acetonitrile solution, and hydroxylamine hydrochloride (218 mg, 3.1 mmol) and triethylamine (0.55 mL, 3.9 mmol) were added at 0° C. to obtain a mixture, the mixture was heated for reflux and stirred for 5 h, and the acetonitrile solution was removed by rotary evaporation to obtain 468 mg of Compound 8.

Compound 8 (468 mg, 2.6 mmol) was dissolved in 8 mL of dimethyl sulfoxide solution under ice bath conditions, potassium carbonate (880 mg, 6.3 mmol) and acetic anhydride (0.6 mL, 6.3 mmol) were then added to obtain a mixture, the mixture was heated and stirred at 50° C. overnight, quenched with water, extracted with dichloromethane and then dried with anhydrous sodium sulfate, the dimethyl sulfoxide solution was removed by rotary evaporation, and column chromatography was performed to obtain 375 mg of a white solid, that is, Compound A-3, with a yield of 88% over two steps. $^1$H NMR (500 MHz, $CDCl_3$) δ 8.31 (s, 1H), 3.83 (s, 3H), 2.46 (s, 3H), 2.32 (s, 3H). ESI-HRMS: $[M+H]^+$ calcd. For$[C_9H_{11}N_2O]^+$ m/z: 163.0866; found: 163.0863.

Step 3: Preparing Compound Tz-17

Compound A-3 (34 mg, 0.2 mmol) and 2-cyanopyridine (83 mg, 0.8 mmol) were dissolved in 2 mL of ethanol solution in a nitrogen atmosphere, 3-mercaptopropionic acid (0.01 mL, 0.08 mmol) was added first at 0° C., hydrazine hydrate (0.16 mL, 3.2 mmol) was then slowly added dropwise to obtain a mixture, and the mixture was heated to 40° C. and stirred for 24 h for reaction. After the mixture was cooled to room temperature, sodium nitrite and hydrochloric acid were added to the mixture under ice bath conditions and stirred for 30 min, extracted with dichloromethane, and dried with anhydrous sodium sulfate, the ethanol solution was removed by rotary evaporation, and column chromatography was performed to obtain 10 mg of a purple-red solid, that is, Compound Tz-17, with a yield of 21%. A nuclear magnetic resonance spectrum was shown in FIG. 1. $^1$H NMR (400 MHz, $CDCl_3$) δ 8.99 (d, J=4.7 Hz, 1H), 8.75 (d, J=7.9 Hz, 1H), 8.56 (s, 1H), 8.02 (td, J=7.8, 1.7 Hz, 1H), 7.70-7.54 (m, 1H), 3.89 (s, 3H), 2.52 (s, 3H), 2.41 (s, 3H). ESI-HRMS: $[M+H]^+$ calcd. For $[C_{15}H_{15}N_6O]^+$ m/z: 295.1302; found: 295.1296.

Example 3

Preparation of Compound Tz-30

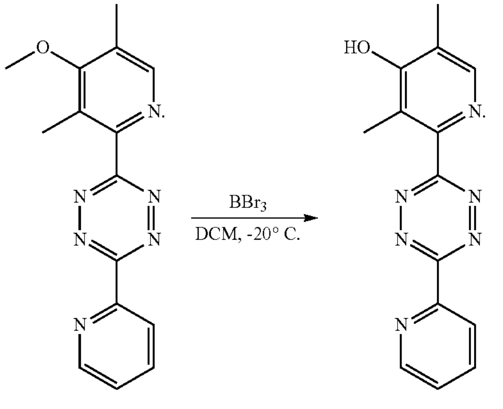

Tz-17 Tz-30

Compound Tz-17 (30 mg, 0.1 mmol) was dissolved in 1 mL of dichloromethane solution in a nitrogen atmosphere, boron tribromide solution (1 mL, 1 mmol) was slowly added dropwise at −20° C., the reaction was allowed to continue for 12 h after the addition was completed, the reaction was slowly quenched with methanol solution, dichloromethane was removed by rotary evaporation, and column chromatography was performed to obtain 9 mg of a red solid, that is, Compound Tz-30, with a yield of 30%. $^1$H NMR (500 MHz, Methanol-d4) δ 8.91 (dt, J=4.52, 1.49 Hz, 1H), 8.82 (dt, J=7.90, 1.02 Hz, 1H), 8.20 (td, J=7.80, 1.72 Hz, 1H), 7.99 (d, J=1.02 Hz, 1H), 7.77 (ddd, J=7.72, 4.79, 1.19 Hz, 1H), 2.53 (s, 3H), 2.20 (d, J=0.86 Hz, 3H). ESI-HRMS: $[M+H]^+$ calcd. For $[C_{14}H_{13}N_6O]^+$ m/z: 281.1145; found: 281.1140.

The following tetrazine compounds were synthesized using the above preparation method:

Tz-1: a purplish-red solid, $^1$H NMR (500 MHz, Chloroform-d) δ 8.73-8.67 (m, 2H), 8.62 (d, J=5.54 Hz, 1H), 7.68-7.60 (m, 3H), 6.98 (d, J=5.59 Hz, 1H), 4.00 (s, 3H), 2.43 (s, 3H). ESI-HRMS: $[M+H]^+$ calcd. For $[C_{15}H_{14}N_5O]^+$ m/z: 208.1193; found: 280.1189.

Tz-16: a purplish-red solid, $^1$H NMR (500 MHz, Chloroform-d) δ 8.71-8.67 (m, 2H), 8.54 (s, 1H), 7.70-7.60 (m, 3H), 3.89 (s, 3H), 2.54 (s, 3H), 2.40 (s, 3H). ESI-HRMS: $[M+H]^+$ calcd. For $[C_{16}H_{16}N_5O]^+$ m/z: 294.1349; found: 294.1344.

Tz-27: a purplish-red solid, $^1$H NMR (400 MHz, Chloroform-d) δ 8.57 (s, 1H), 5.17 (s, 2H), 3.92 (s, 3H), 3.66 (s, 3H), 2.49 (s, 3H), 2.42 (d, J=0.71 Hz, 3H). ESI-HRMS: $[M+H]^+$ calcd. For $[C_{12}H_{16}N_5O_2]^+$ m/z: 262.1299; found: 262.1295.

Tz-29: a purplish-red solid, $^1$NMR (500 MHz, DMSO-$d_6$) δ 8.64-8.53 (m, 2H), 7.98 (s, 1H), 7.85-7.66 (m, 3H), 2.32 (s, 3H), 2.09 (s, 3H). ESI-HRMS: $[M+H]^+$ calcd. For $[C_{15}H_{14}N_5O]^+$ m/z: 280.1193; found: 280.1188.

Example 4

A method for preparing Compound Tz-28, including the following steps:

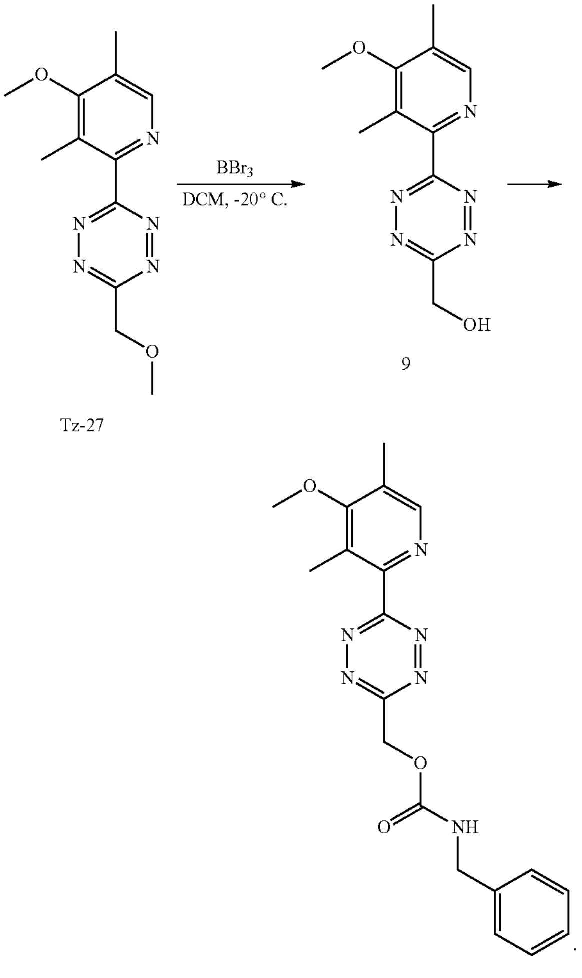

Tz-27 9 Tz-28

Step 1: Preparing Compound 9

Compound Tz-27 (100 mg, 0.38 mmol) was dissolved in 1 mL of dichloromethane solution in a nitrogen atmosphere, boron tribromide solution (2 mL, 2 mmol) was slowly added dropwise at −20° C., the reaction was allowed to continue for 10 h after the addition was completed, the reaction was slowly quenched with methanol solution, reaction solution was removed by rotary evaporation, and column chromatography was performed to obtain 40 mg of a red solid, that is, Compound 9, with a yield of 70%. $^1$H NMR (400 MHz, $CDCl_3$) δ 8.53 (s, 1H), 5.37 (s, 2H), 3.89 (s, 3H), 2.46 (s, 3H), 2.40 (s, 3H). ESI-HRMS: $[M+H]^+$ calcd. For $[C_{10}H_{12}N_5O_2]^+$ m/z: 234.0986; found: 234.0979.

Step 2: Preparing Compound Tz-28

Compound 9 (40 mg, 0.16 mmol) and benzyl isocyanate (27 mg, 0.2 mmol) were dissolved in 1 mL of dichloromethane solution in a nitrogen atmosphere, triethylamine (20 mg, 0.2 mmol) was slowly added dropwise to obtain a mixture, the mixture was reacted at room temperature for 3 h, reaction solution was removed by rotary evaporation, and column chromatography was performed to obtain 24 mg of a red solid, that is, Compound Tz-28, with a yield of 40%. $^1H$ NMR (400 MHz, $CDCl_3$) δ 8.52 (s, 1H), 7.38-7.26 (m, 5H), 5.80 (s, 2H), 5.41 (s, 1H), 4.43 (d, J=5.9 Hz, 2H), 3.88 (s, 3H), 2.47 (s, 3H), 2.39 (s, 3H). ESI-HRMS: $[M+H]^+$ calcd. For $[C_{18}H_{19}N_6O_3]^+$ m/z: 367.1513; found: 367.1508.

Similarly, Compound Tz-13 could be prepared by replacing the raw material with Compound Tz-12.

Yields of the following synthesize tetrazine compounds were as follows using the above preparation method:

| Compound 1 | Compound 2 | Product | Yield |
|---|---|---|---|
| A-1 | B-1 | Tz-1 | 46% |
| A-1 | B-3 | Tz-3 | 26% |
| A-1 | B-4 | Tz-4 | 26% |
| A-1 | B-5 | Tz-5 | 25% |
| A-1 | B-6 | Tz-6 | 26% |
| A-1 | B-7 | Tz-7 | 26% |
| A-1 | B-8 | Tz-8 | 28% |
| A-1 | B-9 | Tz-9 | 40% |
| A-1 | B-10 | Tz-10 | 35% |
| A-1 | B-11 | Tz-11 | 33% |
| A-1 | B-12 | Tz-12 | 30% |
| A-1 | B-13 | Tz-13 | 30% |
| A-2 | B-1 | Tz-14 | 22% |
| A-2 | B-2 | Tz-15 | 23% |
| A-3 | B-1 | Tz-16 | 28% |
| A-3 | B-3 | Tz-18 | 22% |
| A-3 | B-4 | Tz-19 | 23% |
| A-3 | B-5 | Tz-20 | 26% |
| A-3 | B-6 | Tz-21 | 26% |
| A-3 | B-7 | Tz-22 | 27% |
| A-3 | B-8 | Tz-23 | 28% |
| A-3 | B-9 | Tz-24 | 26% |
| A-3 | B-10 | Tz-25 | 28% |
| A-3 | B-11 | Tz-26 | 25% |
| A-3 | B-12 | Tz-27 | 30% |
| A-4 | B-1 | Tz-29 | 26% |

Example 5

Preparation of Compound 10

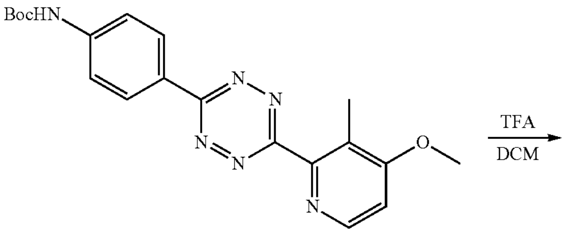

Tz-10

-continued

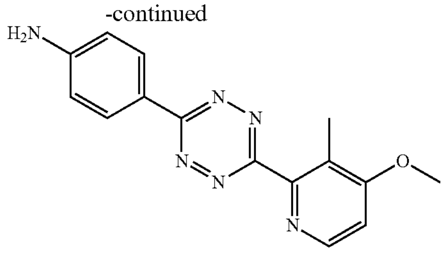

10

Compound Tz-10 (0.10 g, 0.25 mmol) was dissolved in 1 mL of DCM, 0.5 mL of trifluoroacetic acid was slowly added dropwise at 0° C. to obtain a mixture, the mixture was reacted for 30 min, and reaction solution was removed by rotary evaporation, and column chromatography was performed to obtain 30 mg of a brown-red solid, that is, Compound 10, with a yield of 40%. $^1H$ NMR (500 MHz, Methanol-$d_4$) δ 8.67 (d, J=6.44 Hz, 1H), 8.44-8.31 (m, 2H), 7.56 (d, J=6.47 Hz, 1H), 6.86-6.71 (m, 2H), 4.21 (s, 3H), 2.56 (s, 3H). ESI-HRMS: $[M+H]^+$ calcd. For $[C_{15}H_{15}N_6O]^+$ m/z: 295.1302; found: 295.1298.

Example 6

Preparation of Styryl Boronic Acid Derivative VBA-1

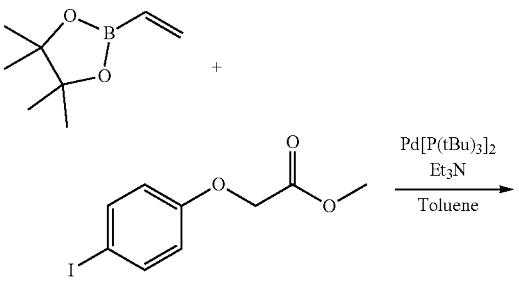

11

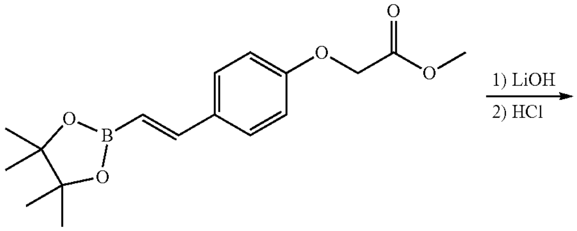

12

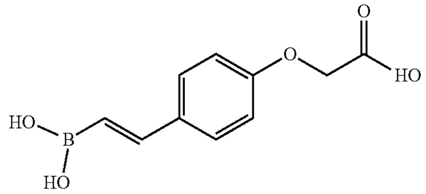

VBA-1

Compound 11 (8.0 g, 20 mmol) and vinylboronic pinacol ester (3.7 mL, 22 mmol) and $Pd[P(tBu)_3]_2$ (0.5 g, 1 mmol) were added in anhydrous toluene (100 mL) in a nitrogen atmosphere, triethylamine (6 mL, 40 mmol) was then added to obtain a mixture, and the mixture was heated at 50° C. and stirred overnight; and after overnight reaction, reaction solution was removed by rotary evaporation, and column chromatography was performed to obtain 6.3 g of a white solid, that is, Compound 12, with a yield of 73%. $^1$H NMR (400 MHz, Chloroform-d) δ 7.63-7.43 (m, 2H), 6.76-6.57 (m, 2H), 4.60 (s, 2H), 3.79 (s, 3H). ESI-HRMS: $[M+H]^+$ calcd. For $[C_{17}H_{24}BO_5]^+$ m/z: 319.1711; found: 319.1706.

Compound 12 (0.32 g, 1 mmol) and lithium hydroxide (48 mg, 2 mmol) was dissolved in mixed solution composed of 4 mL THE and 1 mL water to obtain a mixture, the mixture was stirred at room temperature for 2 h, liquid was evaporated by rotary evaporation, a small amount of dilute hydrochloric acid (with a concentration of 0.5 M) was added and stirred for 30 min, and column chromatography was performed to obtain 1.3 g of a light yellow solid, that is, Compound VBA-1, with a yield of 60%. $^1$H NMR (400 MHz, Methanol-$d_4$) δ 7.50-7.38 (m, 2H), 7.28 (d, J=18.11 Hz, 1H), 6.96-6.86 (m, 2H), 6.22 (d, J=18.07 Hz, 1H), 4.67 (s, 2H). ESI-HRMS: $[M-H]^-$ calcd. For $[C_{10}H_{10}BO_5]^-$ m/z: 221.0627; found: 221.0623.

Example 7

Preparation of Styryl Boronic Acid Derivative VBA-2

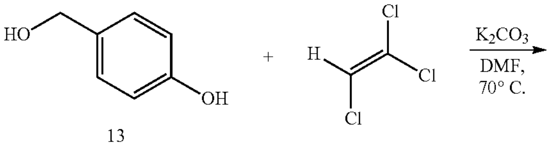

13

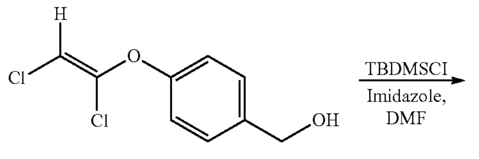

14

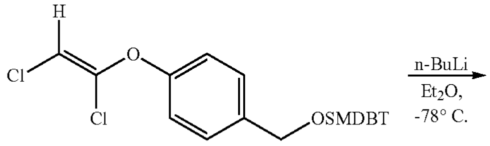

15

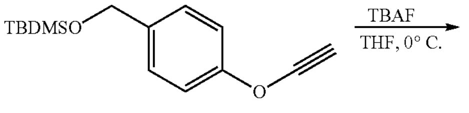

16

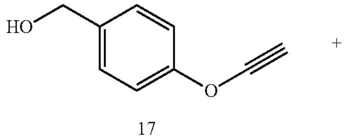

17

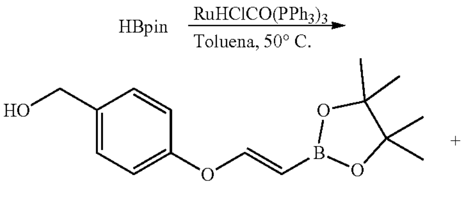

18

-continued

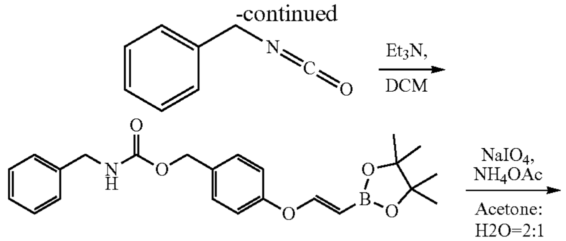

19

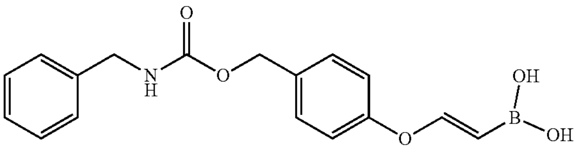

VBA-2

Step 1: Preparing Compound 14

Compound 13 (1.25 g, 10 mmol) and potassium carbonate (1.97 g, 15 mmol) were dissolved in 15 mL of DMF solution, stirred and heated to 70° C. to obtain reaction liquid, and trichloroethylene (2.10 g, 15 mmol) was slowly added dropwise to the reaction liquid for reacting overnight to obtain a mixture; and the mixture was extracted with ethyl acetate solution, and dried with anhydrous sodium sulfate, reaction solution was removed by rotary evaporation, and column chromatography was performed to obtain 2.08 g of light yellow oil, that is, Compound 14, with a yield of 79%. $^1$H NMR (400 MHz, $CDCl_3$) δ 7.41-7.35 (m, 2H), 7.11-6.97 (m, 2H), 5.96 (s, 1H), 4.68 (s, 2H). ESI-HRMS: $[M+H]^+$ calcd. For $[C_9H_9C_{12}O_2]^+$ m/z: 218.9974; found: 218.9969.

Step 2: Preparing Compound 15

Compound 14 (2.08 g, 9.5 mmol) was dissolved in 20 mL of DMF solution, imidazole (0.95 g, 14 mmol) and TBDMSCL (2.11 g, 14 mmol) were added under ice bath conditions to obtain a mixture, and the mixture was reacted for another 4 h to obtain a mixture after returning to room temperature 30 min later; and the mixture was extracted with ethyl acetate solution, and dried with anhydrous sodium sulfate, and column chromatography was performed to obtain 3.00 g of colorless liquid, that is, Compound 15, with a yield of 85%. $^1$H NMR (400 MHz, $CDCl_3$) δ 7.37-7.29 (m, 2H), 7.08-7.00 (m, 2H), 5.94 (s, 1H), 4.72 (s, 2H), 0.95 (s, 9H), 0.11 (s, 6H). ESI-HRMS: $[M+H]^+$ calcd. For $[C_{15}H_{22}Cl_2O_2Si]^+$ m/z: 332.0766; found: 332.0759.

Step 3: Preparing Compound 16

Compound 15 (3.00 g, 9 mmol) was dissolved in 20 mL of anhydrous tetrahydrofuran solution in a nitrogen atmosphere, n-butyl lithium (22 mL, 36 mmol) was slowly added dropwise at −80° C. for reaction for 1 h to obtain a mixture, and the mixture was reacted for another 2 h after a temperature was naturally restored to −40° C.; the reaction was quenched with ice water, the mixture was extracted with ethyl acetate solution, and dried with anhydrous sodium sulfate, and column chromatography was performed to obtain 1.89 g of brown liquid, that is, Compound 16, with a yield of 69%. $^1$H NMR (400 MHz, $CDCl_3$) δ 7.36-7.29 (m, 2H), 7.27-7.23 (m, 2H), 4.72 (s, 2H), 2.07 (s, 1H), 0.93 (s, 9H), 0.09 (s, 6H). ESI-HRMS: $[M+H]^+$ calcd. For $[C_{15}H_{23}O_2Si]^+$ m/z: 263.1462; found: 263.1458.

Step 4: Preparing Compound 17

Compound 16 (0.67 g, 2.55 mmol) was dissolved in 10 mL of tetrahydrofuran solution under ice bath conditions, TBAF (2.8 mL, 2.8 mmol) was added for reaction for 30 min to obtain a mixture, and the mixture was reacted for another 4 h after returning to room temperature; and the tetrahydrofuran solution was removed by rotary evaporation, and column chromatography was performed to obtain 0.34 g of brown liquid, that is, Compound 17, with a yield of 52%. $^1$H NMR (500 MHz, $CDCl_3$) δ 7.41-7.35 (m, 2H), 7.31-7.26 (m, 2H), 4.68 (d, J=5.7 Hz, 2H), 2.10 (s, 1H). ESI-HRMS: $[M+H]^+$ calcd. For $[C_9H_8O_2]^+$ m/z: 148.0524; found: 148.0519.

Step 5: Preparing Compound 18

Compound 17 (0.34 g, 2.3 mmol) was dissolved in 15 mL of toluene solution in a nitrogen atmosphere, ruthenium catalyst (0.11 g, 0.12 mmol) and pinacol borane (1.46 g, 12 mmol) were added to obtain a mixture, and the mixture was heated to 50° C. for overnight reaction; reaction solution was removed by rotary evaporation, and column chromatography was performed to obtain 0.38 g of light yellow liquid, that is, Compound 18, with a yield of 74%. $^1$H NMR (400 MHz, $CDCl_3$) δ 7.36-7.31 (m, 2H), 7.23 (d, J=13.8 Hz, 1H), 7.07-7.02 (m, 2H), 4.88 (d, J=13.9 Hz, 1H), 4.66 (d, J=5.7 Hz, 2H), 1.60 (t, J=5.9 Hz, 1H), 1.27 (s, 12H). ESI-HRMS: $[M+H]^+$ calcd. For $[C_{15}H_{22}BO_4]^+$ m/z: 277.1606; found: 277.1600.

Step 6. Preparing Compound VBA-2

Compound 18 (0.38 g, 1.38 mmol) and benzyl isocyanate (0.20 g, 1.51 mmol) were dissolved in 5 mL of dichloromethane solution in a nitrogen atmosphere, triethylamine (0.15 g, 1.51 mmol) was slowly added dropwise to obtain a mixture, the mixture was reacted at room temperature for 3 h, reaction solution was removed by rotary evaporation, and column chromatography was performed to obtain 0.36 g of Compound 19.

Figure 2:
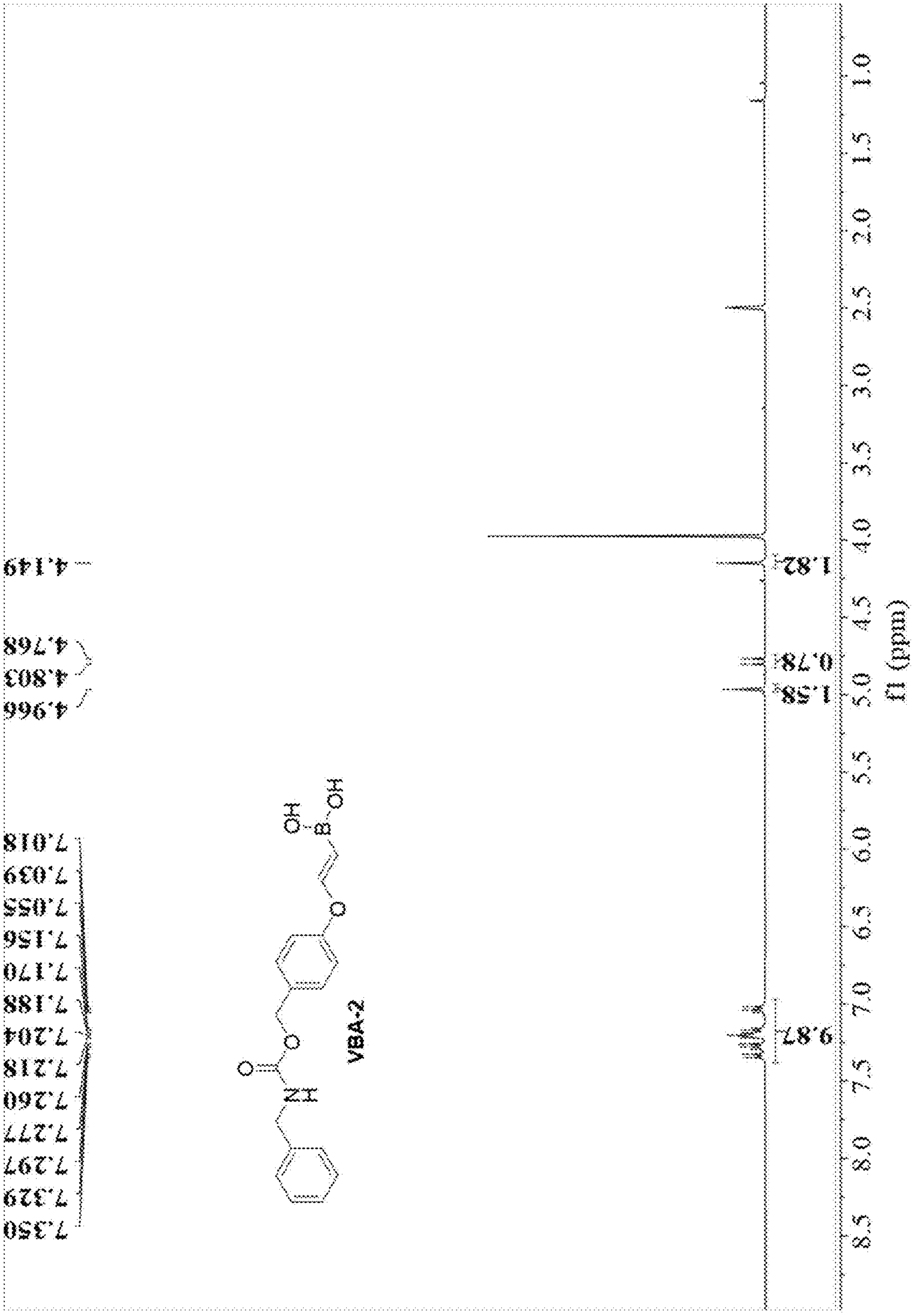
FIG. 2 is a nuclear magnetic resonance spectrum of a prepared olefinic boronic acid derivative VBA-2.

Compound 19 (0.20 g, 0.49 mmol), sodium periodate (0.32 g, 1.5 mmol), and ammonium acetate (0.12 g, 1.5 mmol) were dissolved in mixed solution composed of 4 mL of acetone and 2 mL of water to obtain a mixture, and the mixture was reacted at room temperature for 3 h; and the mixture was extracted with ethyl acetate solution, and dried with anhydrous sodium sulfate, and column chromatography was performed to obtain 0.10 g of a white solid, that is, Compound VBA-2, with a yield of 64%. Nuclear magnetic resonance spectrum was shown in FIG. 2. $^1$H NMR (400 MHz, DMSO) δ 7.39-6.97 (m, 10H), 4.97 (s, 2H), 4.79 (d, J=13.8 Hz, 1H), 4.15 (s, 2H). ESI-HRMS: $[M+H]^+$ calcd. For $[C_{17}H_{18}BNO_5]^+$ m/z: 327.1278; found: 327.1271.

Example 8

Preparation of Doxorubicin Prodrug DOX-VBA

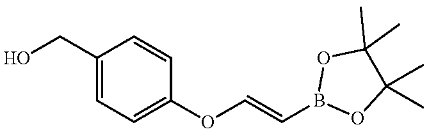

18

+

-continued

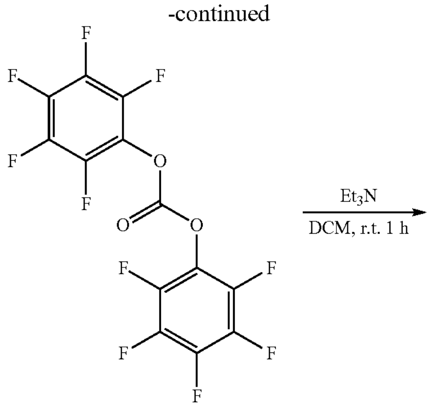

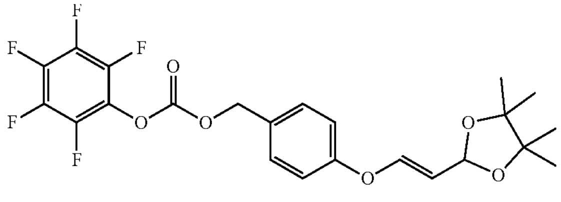

20

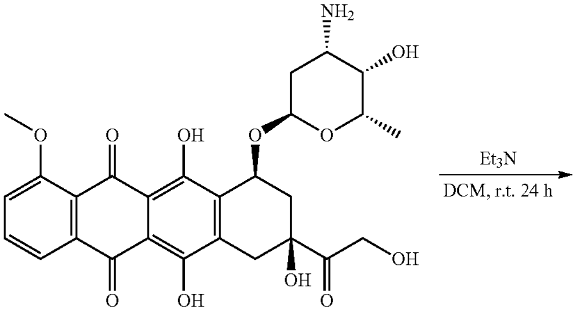

DOX-HCl

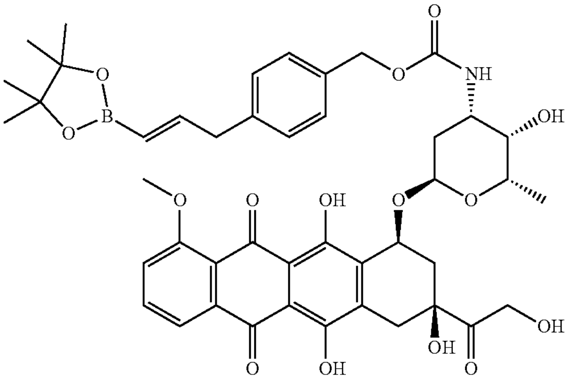

DOX-VBA

Figure 3:
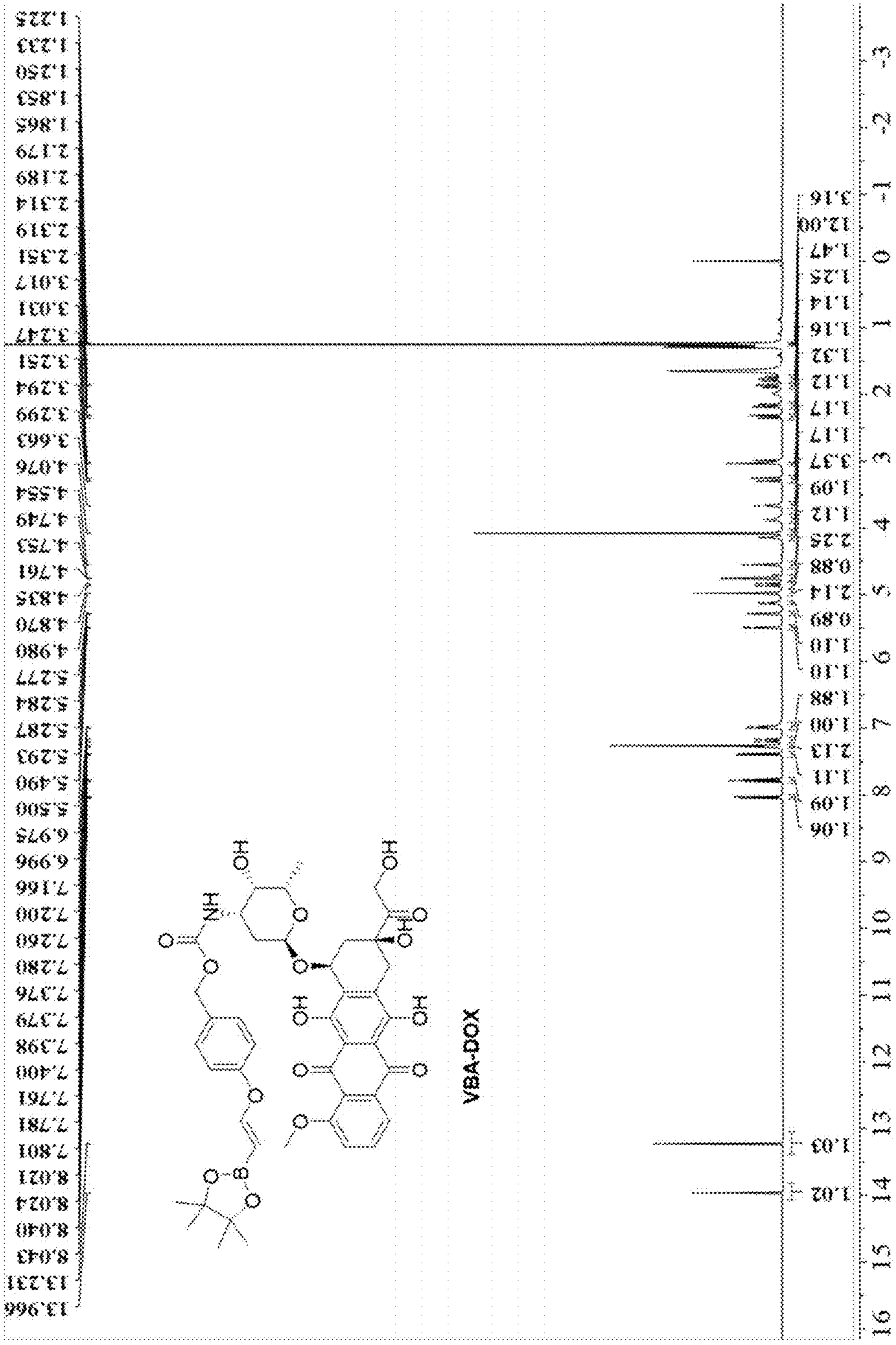
FIG. 3 is a nuclear magnetic resonance spectrum of a prepared doxorubicin prodrug DOX-VBA.

Compound 18 (0.036 g, 0.13 mmol) and bis(perfluorophenyl)carbonate (0.20 g, 1.51 mmol) were dissolved in 5 mL of dichloromethane solution in a nitrogen atmosphere, triethylamine (0.055 g, 0.14 mmol) was then slowly added dropwise to obtain a mixture, the mixture was reacted at room temperature for 3 h, reaction solution was removed by rotary evaporation to obtain a crude product of Compound 20, and the next step was then performed. The crude product of Compound 20, doxorubicin hydrochloride (0.075 g, 0.13 mmol), and triethylamine (0.015 g, 0.15 mmol) were dissolved in 4 mL of anhydrous dry DMF solution, and reacted at room temperature for 24 h to obtain a mixture. The mixture was then extracted with dichloromethane and water, and an organic phase was dried over anhydrous sodium sulfate; and after concentration, column chromatography was performed to obtain 0.031 g of a red solid, that is, Compound DOX-VBA, with a yield of 30% over two steps. Nuclear magnetic resonance spectrum was shown in FIG. 3. $^1$H NMR (400 MHz, Chloroform-d) δ 13.97 (s, 1H), 13.23 (s, 1H), 8.03 (dd, J=7.71, 1.08 Hz, 1H), 7.78 (t, J=8.10 Hz, 1H), 7.39 (dd, J=8.65, 1.09 Hz, 1H), 7.27 (d, J=8.14 Hz, 2H), 7.18 (d, J=13.80 Hz, 1H), 6.99 (d, J=8.16 Hz, 2H), 5.50 (d, J=3.89 Hz, 1H), 5.29 (q, J=2.60 Hz, 1H), 5.13 (d, J=8.58 Hz, 1H), 4.98 (s, 2H), 4.85 (d, J=13.84 Hz, 1H), 4.81-4.70 (m, 2H), 4.55 (s, 1H), 4.14 (d, J=6.60 Hz, 1H), 4.08 (s, 3H), 3.88 (d, J=12.49 Hz, 1H), 3.66 (s, 1H), 3.27 (dd, J=18.87, 1.92 Hz, 1H), 3.02 (d, J=5.69 Hz, 1H), 2.33 (dt, J=14.85, 2.16 Hz, 1H), 2.17 (dd, J=14.74, 4.07 Hz, 1H), 1.88 (dd, J=13.52, 5.07 Hz, 1H), 1.77 (td, J=13.16, 4.05 Hz, 1H), 1.25 (s, 12H), 1.23 (s, 3H). ESI-HRMS: $[M+H]^+$ calcd. For $[C_{43}H_{49}BNO_{16}]^+$ m/z: 846.3139; found: 846.3130.

Example 9

Stability Testing of Tetrazine Compounds

Specific implementation method: The tetrazine compounds were respectively dissolved in a 10% FBS/DMEM solution at a concentration of 100 M (the solution contained 2.5% DMSO as a solubilizing agent), and residual amounts of tetrazine compounds were monitored via HPLC after 6 hours and 24 hours to analyze the stability of tetrazine compounds in a biological environment.

| | Tz-Py | Tz-2 | Tz-1 | Tz-16 | Tz-10 | Tz-11 |
|---|---|---|---|---|---|---|
| 6 h | 35% | 55% | 99% | 99% | 99% | 99% |
| 24 h | 1% | 17% | 85% | 90% | 92% | 92% |

A structure of Tz-Py is shown as follows:

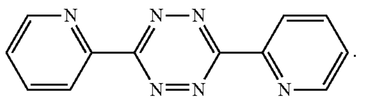 [SMILES: c1ccc(-c2nnc(-c3ccccn3)nn2)nc1]

As the commonly used tetrazine compounds in the prior art, they are used for comparison with the tetrazine compounds of the present disclosure.

The test results indicate that 92% of the tetrazine compounds of the present disclosure was undamaged in biological environments after 24 hours. Compared with the prior art, stability of the tetrazine compounds of the present disclosure have improved in the biological environments.

Example 10

Reaction Rate Testing of Tetrazine Compounds and Styryl Boronic Acid

Specific implementation method: HPLC was used to test reaction rates by monitoring residual amounts of tetrazine compounds after different tetrazine compounds reacted with styryl boronic acid, where a molar concentration of the tetrazine compounds was 1 mM, and a molar concentration of styryl boronic acid was 0.2 mM, and a solvent was methanol solution.

| | Tz-Py | Tz-2 | Tz-1 | Tz-16 | Tz-10 | Tz-11 |
|---|---|---|---|---|---|---|
| $k_2(M^{-1} s^{-1})$ | 1.4 | 168 | 56 | 28 | 45 | 23 |

Test results indicated that a reaction rate of the tetrazine compounds of the present disclosure could reach up to two orders of magnitude compared with the tetrazine compound Tz-Py in the prior art. Furthermore, it can be seen from the stability test data that the tetrazine compounds of the present disclosure could not only exhibit stability in biological environments but also meet the required reaction rates for bioorthogonal reactions, indicating great potential for application in the biomedical field.

Example 11

Molecular Release Testing of Tetrazine Compounds and Styryl Boronic Acid Derivative VBA-2.

Figure 4:
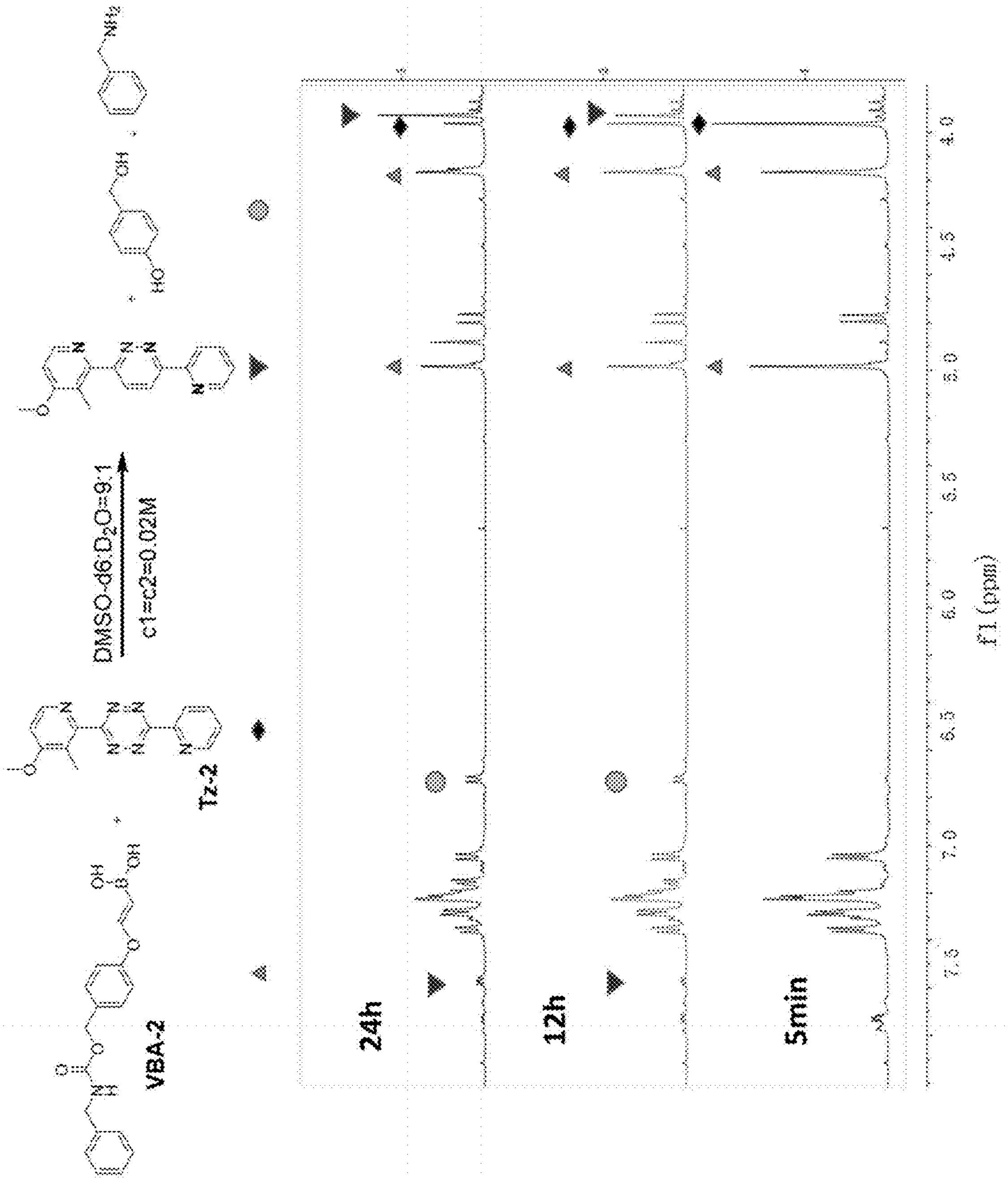
FIG. 4 shows molecular release experimental data of a novel tetrazine compound and an olefinic boronic acid derivative prepared according to the present disclosure.

Specific implementation method: the tetrazine compound Tz-2 and the styryl boronic acid derivative VBA-2 were dissolved in a deuterated solution (deuterated DMSO:deuterated $H_2O$=9:1) at a molar concentration of 0.02 M. Reactions after 5 min, 12 h and 24 h were tested using a 500 MHz a nuclear magnetic resonance analyzer, and characteristic signal peaks of reactants and products on a hydrogen spectrum were tested to assess molecular release. Test results were shown in FIG. 4.

The test results indicated that the tetrazine compound Tz-2 and the styryl boronic acid derivative VBA-2 could release benzylamine molecules after the reaction, and half of the benzylamine molecules were released in 12 h. Under the condition that the prior art cannot take into account both stability and reactivity, the tetrazine compounds of the present disclosure achieved both stability and reactivity through molecular design and synthesis, and could realize drug release strategy and have great potential in targeted prodrug release, which could be expected to be used in the biomedical field.

Example 12

Prodrug Release Strategy Testing

Figure 5:
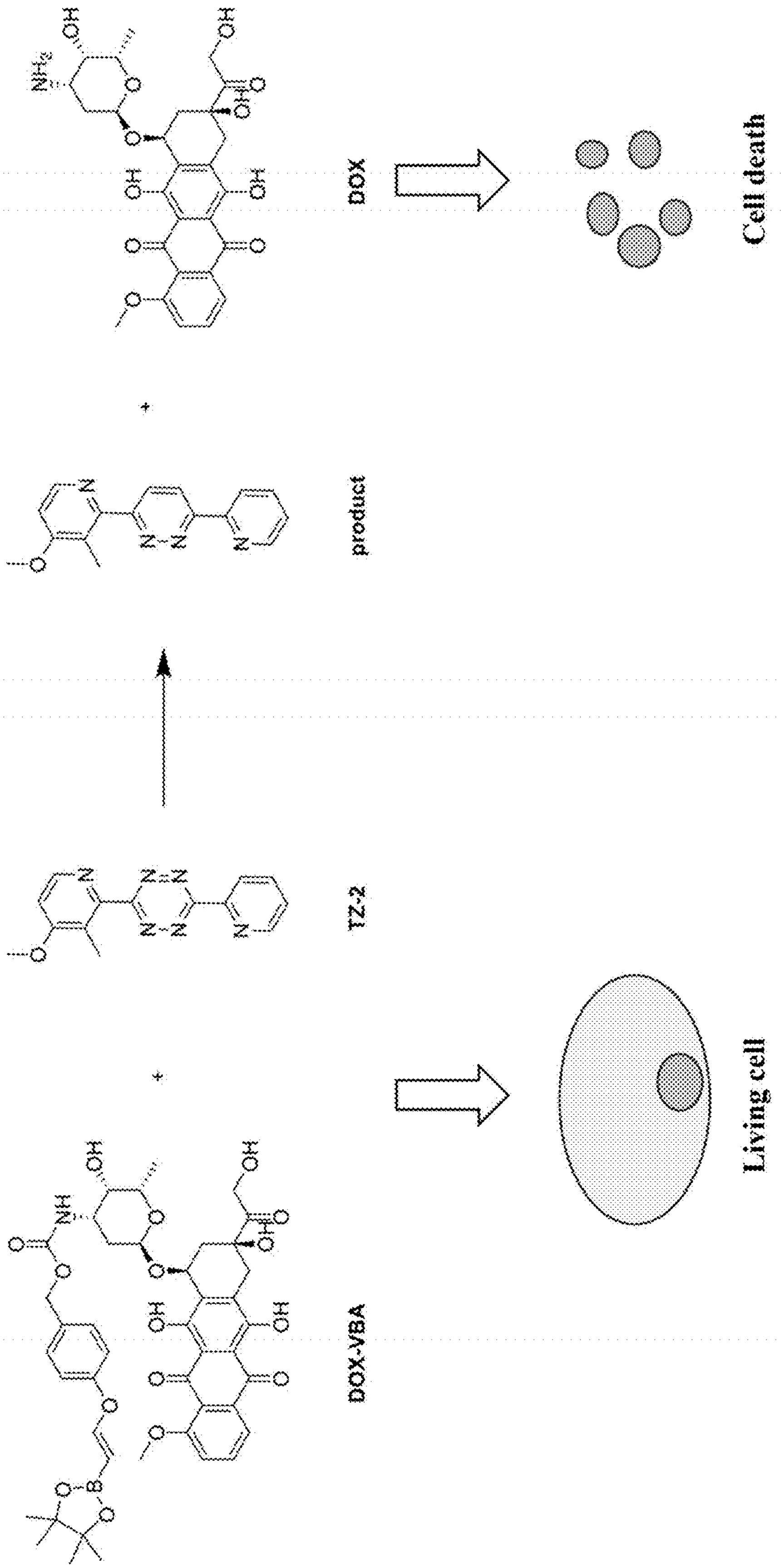
FIG. 5 shows a schematic diagram and a specific molecular structure according to the present disclosure applied to a prodrug release strategy.

Toxicity of the tetrazine Tz-2, the doxorubicin prodrug DOX-VBA, the addition product, and the doxorubicin DOX were first tested. (characterized by $IC_{50}$ value; and molecular structures and schematic diagrams thereof were shown in FIG. 5).

Figure 6:
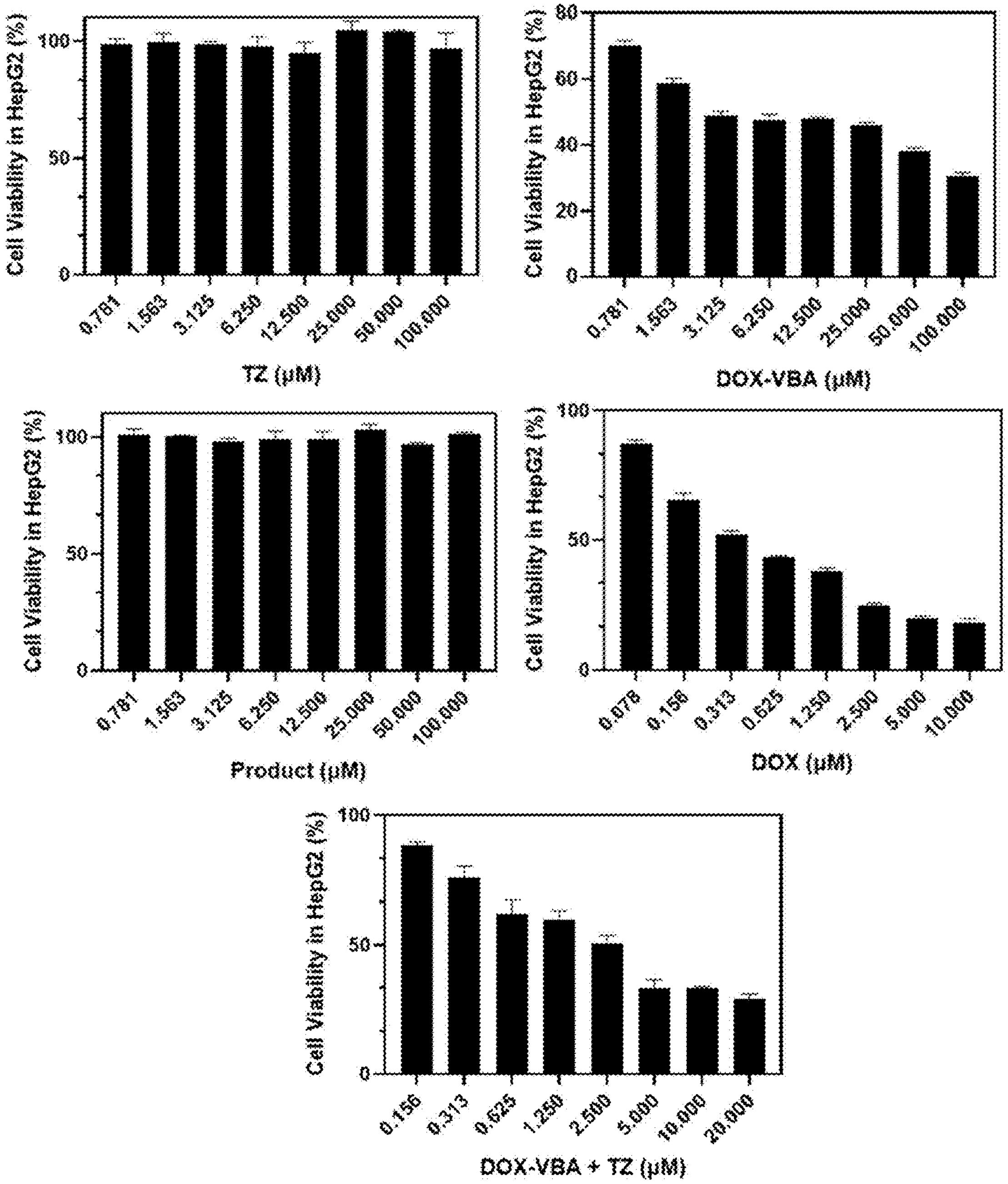
FIG. 6 shows cell survival rates under the conditions of each experimental group.

HepG2 cells were plated in a 96-well plate and attached overnight; 1% FBS DMEM was used as a culture medium on the next day, different concentrations of Tz-2, DOX-VBA, product, and DOX were then added to the culture medium, and incubation was performed at 37° C. for 48 h; and 50 μL 1×MTT was added, the reaction continued for 4 h, DMSO was added to remove the culture medium, and cell survival rates at different concentrations were tested to calculate $IC_{50}$ values (the cell survival rates were shown in FIG. 6).

The prodrug release cell experiments of tetrazine Tz-2 and the doxorubicin prodrug DOX-VBA were then performed.

HepG2 cells were plated in a 96-well plate and attached overnight; 1% FBS DMEM was used as a culture medium on the next day, different concentrations of DOX-VBA were then added to the culture medium, incubation was performed at 37° C. for 30 min, and Tz-2 was then added and incubated for 48 h; and 50 μL 1×MTT was added, the reaction continued for 4 h, DMSO was added to remove the culture medium, and cell survival rates at different concentrations were tested to calculate $IC_{50}$ values (the cell survival rates were shown in FIG. 6).

Gradient Concentrations of Various Compounds in the Prodrug Release Strategy

| Gradient concentration | Tz-2 (μM) | DOX-VBA (μM) | Product (μM) | DOX (μM) |
|---|---|---|---|---|
| 1 | 100 | 100 | 10 | 100 |
| 2 | 50 | 50 | 5 | 50 |
| 3 | 25 | 25 | 2.5 | 25 |
| 4 | 12.5 | 12.5 | 1.25 | 12.5 |
| 5 | 6.25 | 6.25 | 0.625 | 6.25 |
| 6 | 3.125 | 3.125 | 0.312 | 3.125 |
| 7 | 1.562 | 1.562 | 0.156 | 1.562 |
| 8 | 0.781 | 0.781 | 0.078 | 0.781 |

$IC_{50}$ Values of Each Experimental Group in the Prodrug Release Strategy

| | Tz-2 | DOX-VBA | Product | DOX | DOX-VBA + TZ |
|---|---|---|---|---|---|
| $IC_{50}$in HepG2 (μM) | >100 | 6.7 | >100 | 0.5 | 2.3 |

Experimental results indicated that the tetrazine compound Tz-2 and the compound Product were non-toxic and exhibited high biocompatibility. The toxicity of the doxorubicin prodrug was lower than that of doxorubicin. Bioorthogonal reactions were performed to release doxorubicin in situ in the cells, thereby verifying the feasibility of prodrug release at a cellular level.

Example 13

Application of the Tetrazine Compounds and Styryl Boronic Acid Derivatives in Targeted Protein Degradation.

Figure 7:
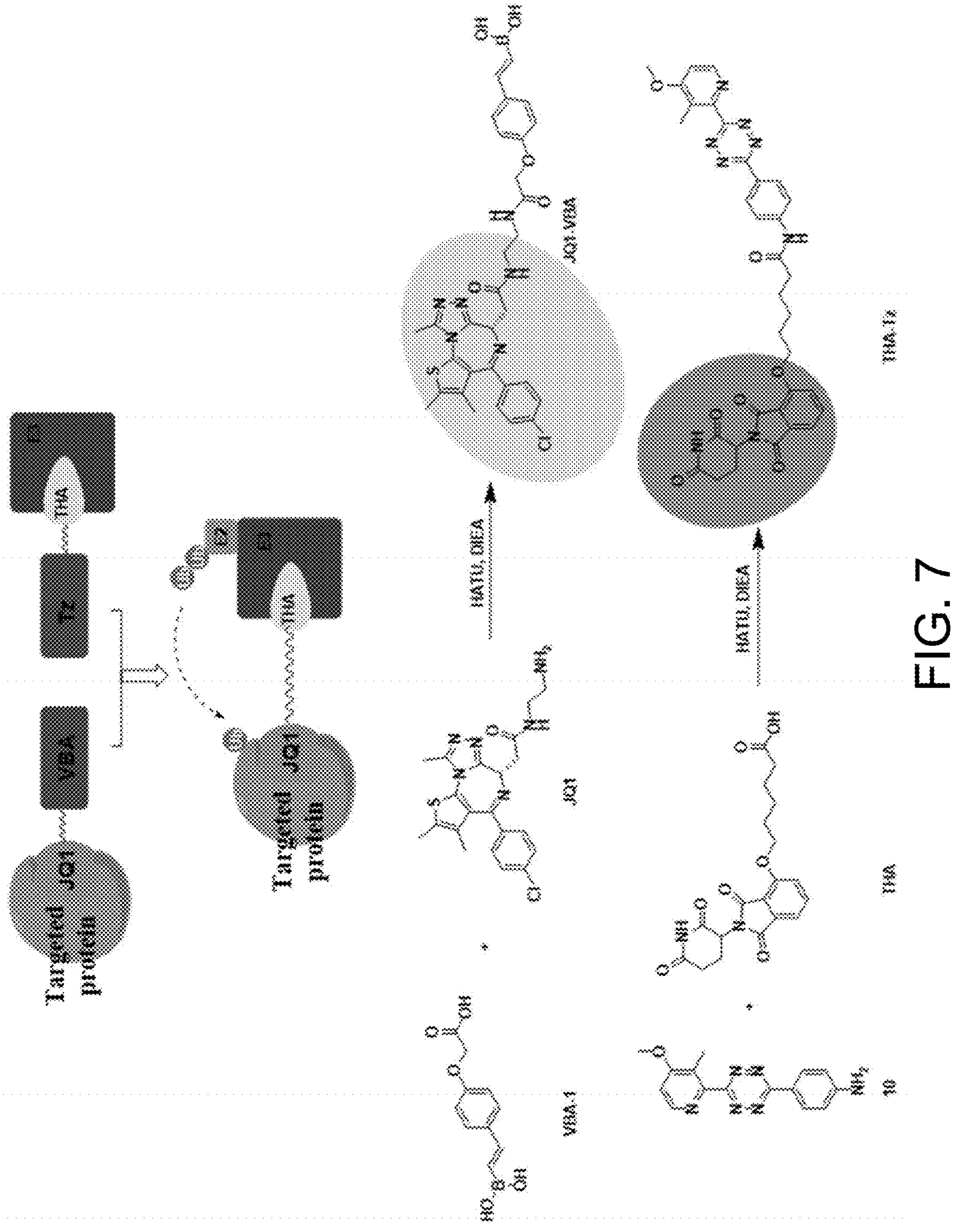
FIG. 7 shows a schematic diagram and a specific molecular structure according to the present disclosure applied to protein-targeted chimera technology.

MDA-MB-231 cells were plated in a 6-well plate and attached overnight; 1% FBS DMEM was used as a culture medium on the next day, and 10 μM of JQ1-VBA (ESI-HRMS: $[M+H]^+_{calcd}$ was added into the culture medium. For$[C_{31}H_{33}BClN_6O_5S]^+$ m/z: 647.2009; found: 647.2002, see FIG. 7; and where JQ1 was a non-covalent inhibitor targeting BRD4 protein, and VBA-1 was used as VBA), and incubation was performed at 37° C. for 18 h. Different concentrations of THA-Tz (ESI-HRMS: $[M+H]^+_{calcd}$. For $[C_{34}H_{33}N_8O_7]^+$ m/z: 665.2467; found: 647.2463 was then added, see FIG. 7; where THA was a ligand thalidomide for CRBN, and the Compound 10 was prepared by removing Boc from Tz-10), the incubation continued for another 20 h at 37° C. The cells were then collected and transferred to a 1.5 mL mold-free centrifuge tube. RIPA lysis buffer was added to ultrasonically lyse the cells on ice. After ultrasonication was completed, the mixture was left on ice for 30 min (vortex once every 10 min), followed by centrifugation at 12,000 g for 5 min at 4° C., a supernatant was then collected, and protein concentration was measured using a BCA kit. 20 μL of 5×SDS loading buffer was taken and added to a 1.5 mL mold-free centrifuge tube, 20 μg of protein solution and a certain volume of lysis buffer were added to bring a final volume up to 100 μL to obtain a mixture, the mixture was thoroughly mixed and placed in a 95° C. metal bath for 5 min, after which a temperature of protein was cooled down to room temperature before the experiment was performed.

Figure 8:
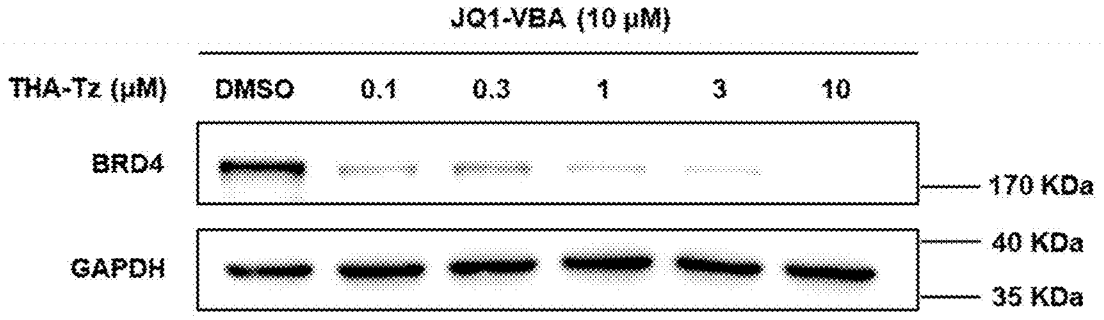
FIG. 8 shows protein band development results of targeted protein degradation.

After successfully separating the proteins in 1×running buffer, the protein was transferred onto a PVDF membrane using pre-cooled 1×trans buffer. Once the transfer was completed, the membrane was blocked in 5% skim milk powder in TBST for 1 h. A target band was then placed in a corresponding primary antibody and incubated at room temperature for 2 h. After incubation with the primary antibody, the membrane was washed 4 times with 1×TBST, 15 min each time. After washing, the membrane was transferred to a corresponding secondary antibody and incubated at room temperature for 1 h, and then washed 4 times with 1×TBST, 15 min each time. Finally, a protein band was developed using a detection kit (see FIG. 8 in details).

Primary Antibody, Secondary Antibody and Dilution Ratios Thereof

| Primary antibody | Dilution ratio of primary antibody | Secondary antibody | Dilution ratio of secondary antibody | Protein size (kDa) |
|---|---|---|---|---|
| BRD4 | 1:1000 | Anti-mouse | 1:2000 | ~200 |
| GAPDH | 1:1000 | Anti-rabbit | 1:2000 | ~37 |

Experimental results demonstrated that two bio-orthogonal precursors with small molecular weight could be used to generate protein degradation targeting chimeras in situ through bio-orthogonal reactions in cells, thereby achieving ubiquitin tagging and efficient degradation of target proteins. The technology has great potential for application in the biomedical field.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A tetrazine compound or a pharmaceutically acceptable salt thereof, wherein a structure of the compound is represented by Formula (I):

I

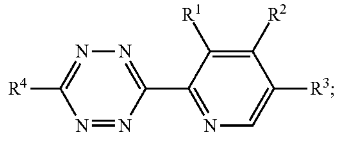

in the formula, $R^1$ is selected from $C_{1-3}$ alkyl;

$R^2$ is selected from hydroxyl, $C_{1-3}$ alkoxy;

$R^3$ is selected from H, $C_{1-3}$ alkyl; and $R^4$ is selected from $C_{1-3}$ alkyl-amino, substituted or unsubstituted phenyl, substituted or unsubstituted six-membered heteroaryl, or $CH_2—O—CH_3$; and the substituted phenyl and the substituted six-membered heteroaryl are each independently substituted by the following groups: amino or $CH_2NH_2$.

2. The tetrazine compound or a pharmaceutically acceptable salt thereof according to claim 1, wherein the six-membered heteroaryl is a six-membered nitrogen heteroaryl; or the amino or the amino in the $C_{1-3}$ alkyl-amino is protected with Boc.

3. The tetrazine compound or a pharmaceutically acceptable salt thereof according to claim 2, wherein the six-membered heteroaryl is pyridyl or pyrimidyl.
4. The tetrazine compound or a pharmaceutically acceptable salt thereof according to claim 1, wherein the tetrazine compound is selected from one of the following structures:
Tz-1
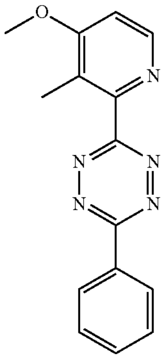
Tz-2
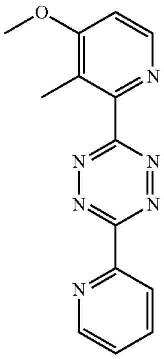
Tz-3
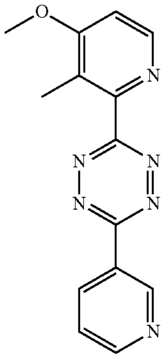
Tz-4
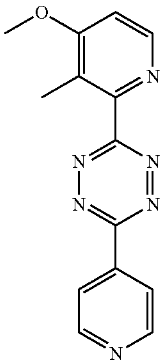
-continued
Tz-5
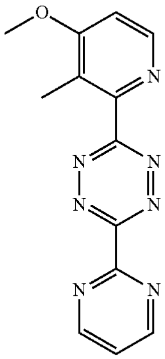
Tz-9
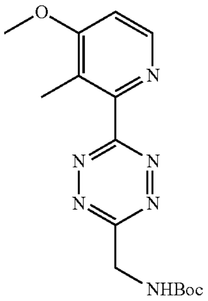
Tz-10
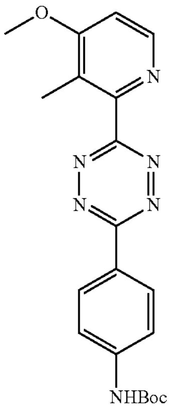
Tz-11
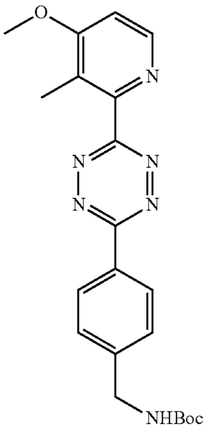

-continued
Tz-12
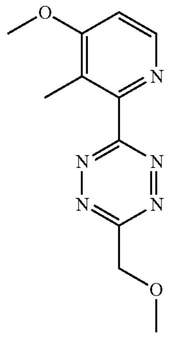
Tz-14
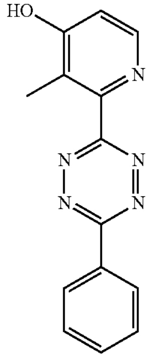
Tz-15
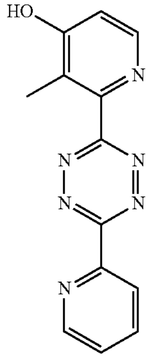
Tz-16
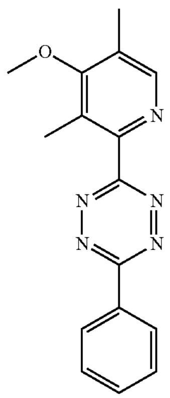
-continued
Tz-17
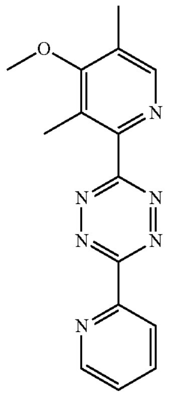
Tz-18
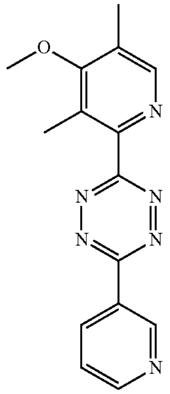
Tz-19
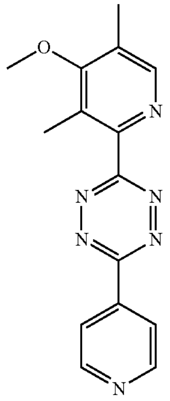
Tz-20
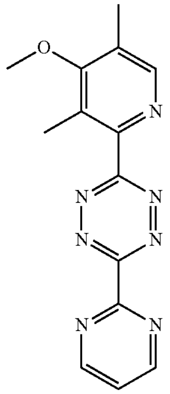

-continued

Tz-24

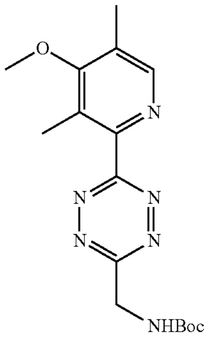

Tz-25

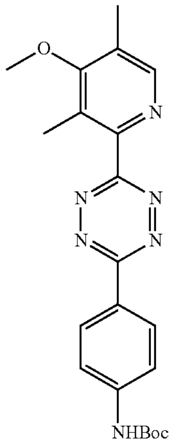

Tz-26

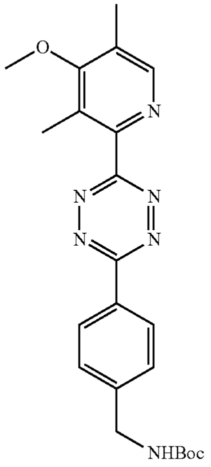

Tz-27

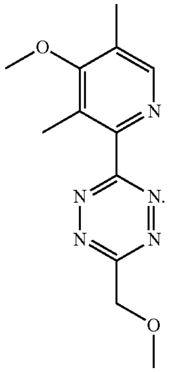

-continued

Tz-29

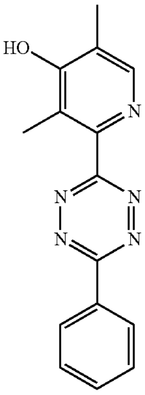

Tz-30

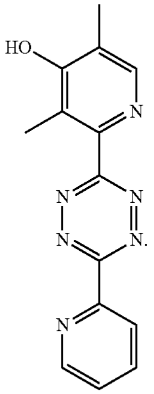

5. A method for preparing the tetrazine compound or a pharmaceutically acceptable salt thereof according to claim 1, comprising the following steps:

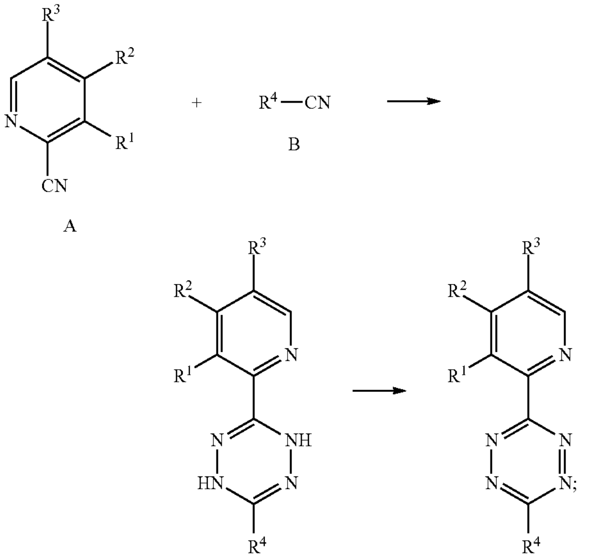

$R^1$, $R^2$, $R^3$ and $R^4$ are the same as described in claim 1.

6. The method for preparing the tetrazine compound or a pharmaceutically acceptable salt thereof according to claim 5, wherein Raw Material A is selected from one of the following structures:

A-1

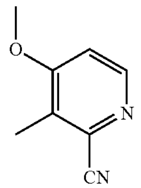

A-2

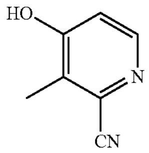

A-3

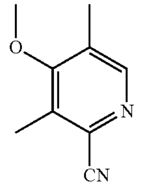

A-4

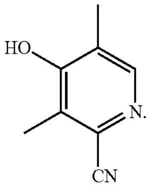

-continued

B-5

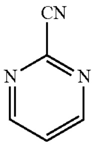

B-9

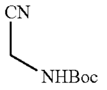

B-10

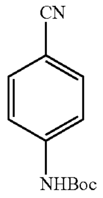

B-11

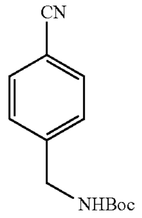

B-12

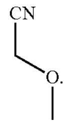

7. The method for preparing the tetrazine compound or a pharmaceutically acceptable salt thereof according to claim 5, wherein Raw Material B is selected from one of the following structures:

B-1

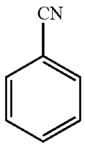

B-2

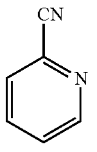

B-3

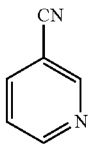

B-4

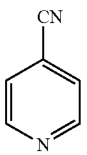

8. A method for preparing the tetrazine compound or a pharmaceutically acceptable salt thereof according to claim 2, comprising the following steps:

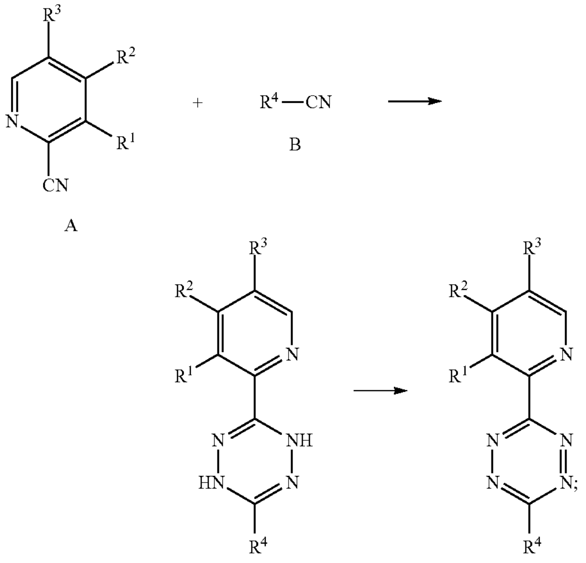

$R^1$, $R^2$, $R^3$ and $R^4$ are the same as described in claim 1.

9. A method for preparing the tetrazine compound or a pharmaceutically acceptable salt thereof according to claim 3, comprising the following steps:

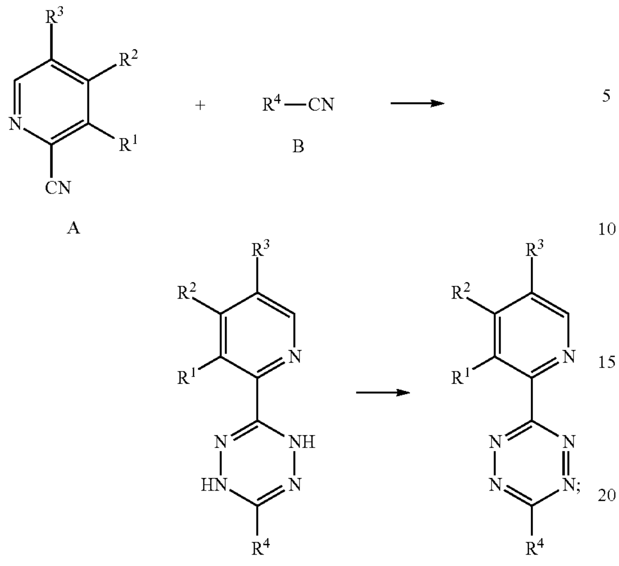
$R^1$, $R^2$, $R^3$ and $R^4$ are the same as described in claim 1.
10. A method for preparing the tetrazine compound or a pharmaceutically acceptable salt thereof according to claim 4, comprising the following steps:
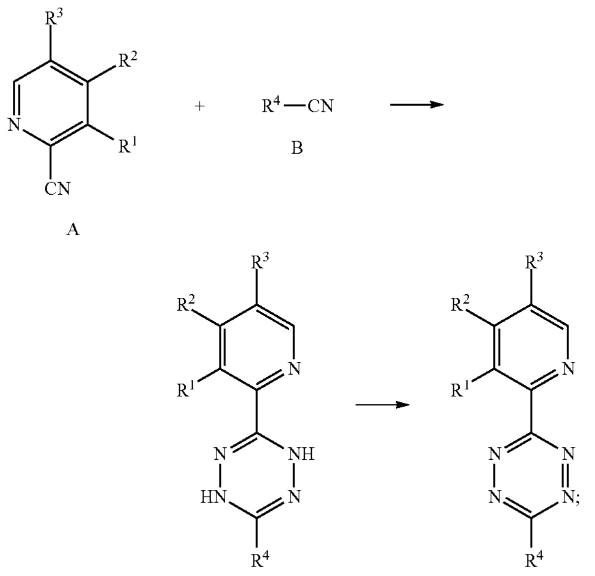
$R^1$, $R^2$, $R^3$ and $R^4$ are the same as described in claim 1.
* * * * *